(12) United States Patent
Porter et al.

(10) Patent No.: US 11,298,506 B2
(45) Date of Patent: Apr. 12, 2022

(54) INTRA-VENTRICULAR INFUSION AND EVACUATION CATHETER FOR TREATMENT OF INTRACEREBRAL HEMORRHAGE (ICH)

(71) Applicants: STRYKER CORPORATION, Kalamazoo, MI (US); STRYKER EUROPEAN OPERATIONS HOLDINGS LLC, Kalamazoo, MI (US)

(72) Inventors: Stephen Porter, Piedmont, CA (US); Jon Schabert, Dublin, CA (US)

(73) Assignees: STRYKER CORPORATION, Kalamazoo, MI (US); STRYKER EUROPEAN OPERATIONS HOLDINGS LLC, Kalamazoo, MI (US)

( * ) Notice: Subject to any disclaimer, the term of this patent is extended or adjusted under 35 U.S.C. 154(b) by 346 days.

(21) Appl. No.: 16/132,861

(22) Filed: Sep. 17, 2018

(65) Prior Publication Data
US 2020/0086083 A1    Mar. 19, 2020

(51) Int. Cl.
*A61M 25/00* (2006.01)
*A61B 17/22* (2006.01)
(Continued)

(52) U.S. Cl.
CPC ... *A61M 25/0068* (2013.01); *A61B 17/22004* (2013.01); *A61M 1/0058* (2013.01); *A61B 2017/22079* (2013.01); *A61B 2017/22084* (2013.01); *A61B 2018/00267* (2013.01); *A61B 2217/005* (2013.01); *A61B 2217/007* (2013.01);
(Continued)

(58) Field of Classification Search
CPC .......... A61B 2017/22079; A61B 2017/22684; A61B 2018/00267; A61B 2217/007; A61M 1/0086; A61M 25/003; A61M 25/0074; A61M 2025/0063; A61M 2025/0036
See application file for complete search history.

(56) References Cited

U.S. PATENT DOCUMENTS

| | | | |
|---|---|---|---|
| 2004/0030281 A1 | 2/2004 | Goble et al. | |
| 2005/0154386 A1* | 7/2005 | West ................. | A61B 18/1492 606/41 |

(Continued)

FOREIGN PATENT DOCUMENTS

WO    WO 01/05450    1/2001

OTHER PUBLICATIONS

PCT International Search Report and Written Opinion for International Appln. No. PCT/US2019/050661, Applicant Stryker Corporation, dated Dec. 11, 2019 (10 pages).

*Primary Examiner* — Rebecca E Eisenberg
*Assistant Examiner* — Tania Ismail
(74) *Attorney, Agent, or Firm* — Vista IP Law Group, LLP

(57) ABSTRACT

A method of treating an anatomical cavity of a patient comprises introducing an infusion/aspiration catheter into the patient, such that a plurality of arms of the catheter reside within the anatomical cavity, delivering a fluid into the at least one of a connector, such that fluid exits the at least one fluid port of at least one of the arms, thereby infusing the anatomical cavity with the fluid, and aspirating the fluid into the at least one fluid port of at least one of the arms, such that the fluid exits the connector(s).

18 Claims, 11 Drawing Sheets

(51) Int. Cl.
*A61M 1/00* (2006.01)
*A61B 18/00* (2006.01)

(52) U.S. Cl.
CPC ....... *A61M 25/003* (2013.01); *A61M 25/0074* (2013.01); *A61M 2025/0036* (2013.01); *A61M 2025/0063* (2013.01); *A61M 2210/0693* (2013.01)

(56) References Cited

U.S. PATENT DOCUMENTS

| | | | |
|---|---|---|---|
| 2006/0004325 A1* | 1/2006 | Hamatake | A61M 1/16 604/43 |
| 2007/0129717 A1* | 6/2007 | Brown, III | A61B 5/015 606/41 |
| 2009/0312807 A1* | 12/2009 | Boudreault | A61F 5/0193 606/86 R |
| 2012/0059309 A1 | 3/2012 | Di Palma et al. | |
| 2012/0232472 A1 | 9/2012 | Bhagchandani et al. | |
| 2014/0324080 A1 | 10/2014 | Wallace | |
| 2015/0173782 A1* | 6/2015 | Garrison | A61F 2/013 606/127 |
| 2016/0166266 A1* | 6/2016 | Nita | A61M 25/104 606/127 |
| 2016/0270806 A1* | 9/2016 | Wallace | A61M 37/0092 |
| 2017/0189040 A1* | 7/2017 | Anand | A61M 1/0058 |
| 2017/0265879 A1* | 9/2017 | Washburn, II | A61B 1/015 |
| 2017/0290598 A1 | 10/2017 | Culbert et al. | |

\* cited by examiner

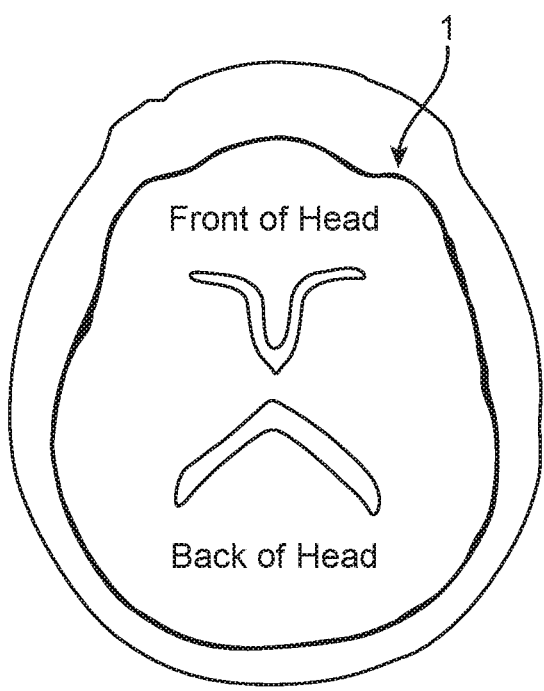
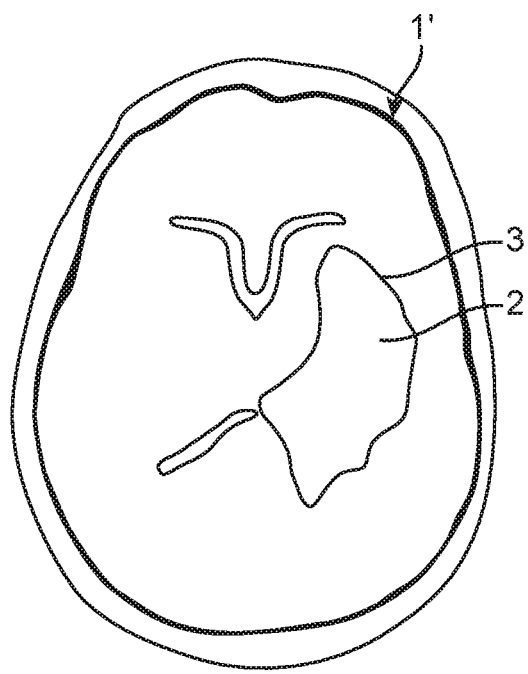
FIG. 1
(PRIOR ART)
FIG. 2
(PRIOR ART)

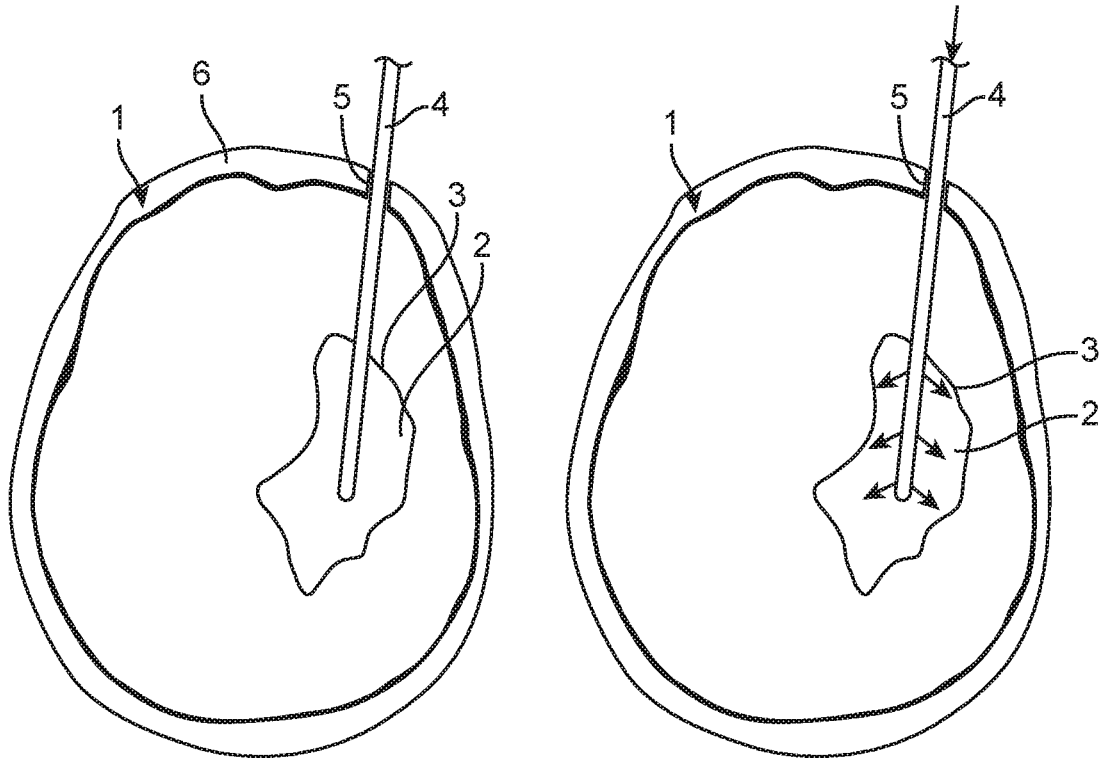
FIG. 3
(PRIOR ART)
FIG. 4
(PRIOR ART)
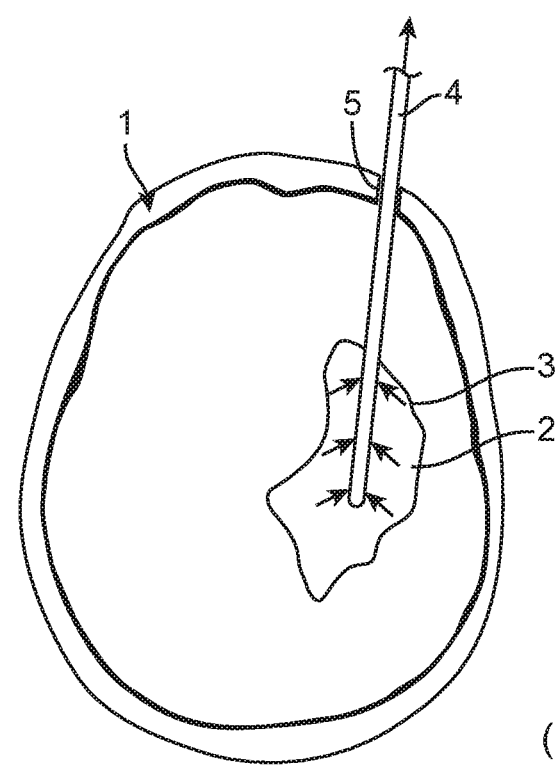
FIG. 5
(PRIOR ART)

INTRA-VENTRICULAR INFUSION AND EVACUATION CATHETER FOR TREATMENT OF INTRACEREBRAL HEMORRHAGE (ICH)

FIELD

The disclosed inventions relate generally to medical devices and intravascular medical procedures and, more particularly, to devices and methods for treating an intracerebral hemorrhage (ICH).

BACKGROUND

Intracerebral hemorrhage (ICH) is a sudden bleeding into brain tissue, which can have devastating results. It is the only major stroke subtype without a clearly effective treatment. ICH occurs in over 100,000 Americans yearly and is fatal in 30-50% of all occurrences, while leaving the majority of survivors with significant motor and cognitive disabilities.

MISTIE (Minimally Invasive Surgery Plus rt-PA for Intracerebral Hemorrhage Evacuation) is a series of clinical trials conducted by neurosurgeons and neurologists to investigate the efficacy of treating ICH by quickly removing blood from the brain through minimally invasive surgery and intermittent dosing of the clot-busting drug, recombinant tissue plasminogen activator (rt-PA). The premise is that by dissolving and removing the clot faster, injury to the brain will be reduced and the patient's prognosis improved.

MISTIE-II, a phase II set of clinical trials for the same purpose, have shown that a blood clot in the brain, can be successfully removed quickly and safely. These early results also suggest that the MISTIE technique may reduce the rate of death, but more significantly, improves the patient's neurologic functioning and quality of life in the year following the occurrence of ICH.

MISTIE-III is an international, phase III 500-patient clinical trial designed to confirm the preliminary findings in a larger number of patients, and has the primary goal of defining a successful treatment for ICH.

FIG. 1 illustrates a computed tomography (CT) scan slice of a normal brain 1' that reveals no ICH, whereas FIG. 2 illustrates a CT scan slice of an abnormal brain 1 that reveals an ICH 2 residing in a ventricle 3 of the brain 1'. The tools used in a MISTIE procedure to treat the ICH 2 are simplistic. In general, a conventional external ventricular drain (EVD) catheter 4 is placed through a standard burr-hole access 5 in the cranium 6 into the ventricle 3 at the site of the ICH 2, as illustrated in FIG. 3. Image guidance may be used Magnetic Resonance (MR)/Computed Tomography (CT), or external anatomical landmarks may be used via standardized methods without image guidance, to target the EVD catheter 4 into the ventricle 3 (using standard ventricular access routes in the case of an intraventricular hemorrhage) at the site of the ICH 2, although the EVD catheter 4 may be targeted to a location outside of the ventricle 3 in the case of an extra-ventricular hemorrhage. In either case, Magnetic Resonance MR/CT imaging is used to confirm correct placement at the site of the ICH 2.

Once correct placement of the EVD catheter 4 is confirmed, an initial bolus of rt-PA is infused in the ventricle 3 at site of the ICH 2 via the EVD catheter 1, and allowed to remain in place for approximately 12-24 hours to dissolve the clot, while the EVD catheter 4 remains open and may be allowed to drain, as illustrated in FIG. 4. Afterwards, remaining fluid (including the rt-PA and dissolved clot) at the site of the ICH 2 is aspirated via the same EVD catheter 1, as illustrated in FIG. 5. This infusion and aspiration process may be repeated at the physician's discretion. The MISTIE procedure, although reasonably effective in treating an ICH, has limitations that are imposed by the simple design of the conventional EVD catheter 4, which was not designed for the purpose of treating an ICH. In particular, the flow of fluid within the conventional EVD catheter 4 can only occur in one direction at a time (either infusion or aspiration, but not both), and furthermore, the rt-PA can only be infused from the EVD catheter 4 in a direction perpendicular to a single straight axis, thereby limiting the administration volume and increasing the diffusive resistance of the rt-PA to reach the entire clot mass. As a result, the time to treat the ICH may be unduly increased.

SUMMARY

In accordance with one aspect of the disclosed inventions, an infusion/aspiration catheter comprises an elongate catheter body having a proximal end, a distal end. The elongate catheter body may, e.g., be sized to be introduced through a burr hole in the cranium of a patient. The infusion/aspiration catheter further comprises a plurality of independent lumens extending between the proximal end and the distal end. The infusion/aspiration catheter further comprises a plurality of arms respectively having proximal ends affixed together at the distal end of elongate catheter body. Each of the arms has a lumen in fluid communication with a respective one of the independent lumens of the elongate catheter body. Each of the arms has at least one fluid port in fluid communication with the lumen of the respective arm. The fluid port(s) may reside, e.g., on an outwardly facing side of the respective arm. A plurality of fluid ports may extend along a length of the respective arm, e.g., on both an outwardly facing side and an inwardly facing side of the respective arm. In one embodiment, the number of arms comprises at least three, and are pre-shaped to expand outward in the absence of an external force.

The infusion/aspiration catheter may further comprise at least one connector affixed to the proximal end of the elongate catheter body in fluid communication with the independent lumens of the elongate catheter body. In one embodiment, the infusion/aspiration catheter comprises a plurality of connectors in fluid communication with the independent lumens of the elongate catheter body. The connectors may be in fluid communication with the respective ones of the independent lumens of the elongated catheter body in a dedicated manner. In one embodiment, the plurality of connectors may comprise a plurality of separate luer connections. In another embodiment, the infusion/aspiration catheter further comprises a manifold assembly comprising the plurality of connectors.

In one embodiment, the infusion/aspiration catheter further comprises a distal hub at which distal ends of the arms are affixed together. In this case, the infusion/aspiration catheter may further comprise an actuation wire having a distal end affixed to the distal hub and a proximal extending from the proximal end of the elongate catheter body. The actuator wire is configured for being proximally displaced relative to the elongate catheter body to expand the plurality of arms outward, and for being distally displaced relative to the elongate catheter body to straighten the plurality of arms.

In another embodiment, the elongate catheter body further has a central lumen extending between the proximal end and distal end of the elongate catheter body, and the independent lumens circumferentially surround the central lumen. In this case, the infusion/aspiration catheter may further comprise another connector affixed to the proximal end of the elongate catheter body in fluid communication with the central lumen of the elongate catheter body in a dedicated manner. The central lumen may have a cross-sectional area greater than a cross-section area of each of the independent lumens. The infusion/aspiration catheter may further comprise a rigid stylet slidably disposed in the central lumen of the elongate catheter body. In this embodiment, the infusion/aspiration catheter may further comprise a distal hub at which distal ends of the arms are affixed together. The distal hub comprises an aperture through which the rigid stylet is disposed.

In accordance with another aspect of the disclosed inventions, the catheter assembly may itself comprise a infusion/aspiration catheter, and an introducer cannula having a lumen through which the infusion/aspiration catheter can be introduced into a target region of a body.

In accordance with yet another aspect of the disclosed inventions, an infusion/aspiration system comprises the infusion/aspiration catheter, a fluid source connected to at least one of the connectors, and a vacuum source or drain connected to at least another one of the connectors.

In accordance with still another aspect of the disclosed inventions, a method of treating an anatomical cavity of a patient comprises introducing the infusion/aspiration catheter into the patient (e.g., via a burr hole in the cranium of the patient), such that the plurality of arms reside within the anatomical cavity (e.g., in a ventricle in a head of the patient or a region where clot has displaced brain tissue of the patient), delivering a fluid (e.g., recombinant tissue plasminogen activator (rt-PA)) into the connector(s), such that fluid exits the fluid port(s) of the corresponding arms, thereby infusing the anatomical cavity with the fluid, and aspirating the fluid into the fluid port(s) of at least one of the arms, such that the fluid exits the connector(s). If the patient has clot residing within the anatomical cavity, the infused rt-PA may dissolve the clot, such that the aspirated fluid comprises the rt-PA and the dissolved clot. In one method, a plurality of connectors is in fluid communication with the independent lumens of the elongate catheter body, in which case, the fluid may be simultaneously infused into and aspirated from the anatomical cavity via different ones of the connectors. In another method, the fluid is sequentially infused into and aspirated from the anatomical cavity via the same ones of the connector(s).

In one embodiment, the method further comprises expanding the arms outward within the anatomical cavity. The method may further comprise placing an introducer sheath within the anatomical cavity. The plurality of arms may be pre-shaped to expand outward in the absence of an external force. In this case, introducing the infusion/aspiration catheter into the patient may comprise introducing the infusion/aspiration catheter through the introducer sheath, such that the introducer sheath applies an external force to the plurality of arms to straighten the arms, and deploying plurality of arms from the introducer sheath, such that the external force is released from the plurality of arms, thereby allowing the arms to expand outward. In an alternative method, an actuation wire may be affixed to a distal hub of the infusion/aspiration catheter. The method may further comprise displacing the actuation wire distally relative to the infusion/aspiration catheter to straighten the arms while introducing the infusion/aspiration catheter into the anatomical cavity, and displacing the actuation wire proximally relative to the infusion/aspiration catheter to expand the arms outward within the anatomical cavity. In still another method, the elongate catheter body may further have a central lumen extending between the proximal end and distal end of the elongate catheter body, in which case, introducing the infusion/aspiration catheter into the anatomical cavity may comprise disposing a rigid stylet within the central lumen of the elongate catheter body.

In accordance with yet another aspect of the disclosed inventions, an infusion/aspiration catheter comprises an elongate catheter body having a proximal end, a distal end, at least one infusion lumen. The elongate catheter body may, e.g., be sized to be introduced through a burr hole in the cranium of a patient. The elongate catheter body further has at least one infusion lumen and an aspiration lumen extending between the proximal end and the distal end. The aspiration lumen terminates in a distal fluid port at the distal end of the elongate catheter body. The infusion lumen(s) may circumferentially surround the central lumen. The central lumen may have a cross-sectional area greater than a cross-section area of each of the infusion(s).

The infusion/aspiration catheter may further comprise a plurality of arms respectively having proximal ends affixed together at the distal end of elongate catheter body. The distal fluid port of the elongate catheter body is between the proximal ends of the plurality of arms. Each of the arms has a lumen in fluid communication with a respective one of the independent lumens of the elongate catheter body. Each of the arms has at least one fluid port in fluid communication with the lumen of the respective arm. The fluid port(s) may reside, e.g., on an outwardly facing side of the respective arm. A plurality of fluid ports may extend along a length of the respective arm, e.g., on both an outwardly facing side and an inwardly facing side of the respective arm. In one embodiment, the number of arms comprises at least three, and are pre-shaped to expand outward in the absence of an external force.

The infusion/aspiration catheter further may comprise at least one infusion connector affixed to the proximal end of the elongate catheter body in fluid communication with the infusion lumen(s), and an aspiration connector affixed to the proximal end of the elongate catheter body in fluid communication with the aspiration lumen(s). In one embodiment, the elongate catheter body comprises a plurality of infusion lumens with which the lumens of the plurality of arms are respectively in fluid communication in a dedicated manner, a plurality of infusion connectors in fluid communication with the plurality of infusion lumens in a dedicated manner. In another embodiment, the elongate catheter body comprises a single infusion lumen with which the lumens of the plurality of arms are respectively in fluid communication, and a single connector in fluid communication with the single infusion lumen. In one embodiment, the infusion connector(s) and aspiration connector(s) may comprise a plurality of separate luer connections. In another embodiment, the infusion/aspiration catheter further comprises a manifold assembly comprising the infusion connector(s) and aspiration connector(s).

In one embodiment, the infusion/aspiration catheter further comprises a distal hub at which distal ends of the arms are affixed together. In this case, the infusion/aspiration catheter may further comprise an actuation wire having a distal end affixed to the distal hub and a proximal extending from the proximal end of the elongate catheter body. The actuator wire is configured for being proximally displaced relative to the elongate catheter body to expand the plurality of arms outward, and for being distally displaced relative to the elongate catheter body to straighten the plurality of arms.

The infusion/aspiration catheter may further comprise a rigid stylet slidably disposed in the central lumen of the elongate catheter body. In this embodiment, the infusion/ aspiration catheter may further comprise a distal hub at which distal ends of the arms are affixed together. The distal hub comprises an aperture through which the rigid stylet is disposed.

In accordance with still another aspect of the disclosed inventions, a catheter assembly comprises the infusion/aspiration catheter, and an introducer cannula having a lumen through which the infusion/aspiration catheter can be introduced into a target region of a body.

In accordance with yet another aspect of the disclosed inventions, an infusion/aspiration system comprises the infusion/aspiration catheter, a fluid source connected to at least one of the connectors, and a vacuum source or drain connected to at least another one of the connectors.

In accordance with still another aspect of the disclosed inventions, a method of treating an anatomical cavity of a patient comprises introducing the infusion/aspiration catheter into the patient (e.g., via a burr hole in the cranium of the patient), such that the plurality of arms reside within the anatomical cavity (e.g., in a ventricle in a head of the patient or a region where clot has displaced brain tissue of the patient), delivering a fluid (e.g., recombinant tissue plasminogen activator (rt-PA)) into the infusion connector(s), such that fluid exits the fluid port(s) of the corresponding arms, thereby infusing the anatomical cavity with the fluid, and aspirating the fluid into the distal fluid port of the elongate catheter body, such that the fluid exits the aspiration connector. If the patient has clot residing within the anatomical cavity, the infused rt-PA may dissolve the clot, such that the aspirated fluid comprises the rt-PA and the dissolved clot. In one method, the fluid may be simultaneously infused into and aspirated from the anatomical cavity. In another method, the fluid is sequentially infused into and aspirated from the anatomical cavity.

In one embodiment, the method further comprises expanding the arms outward within the anatomical cavity. The method may further comprise placing an introducer sheath within the anatomical cavity. The plurality of arms may be pre-shaped to expand outward in the absence of an external force. In this case, introducing the infusion/aspiration catheter into the patient may comprise introducing the infusion/aspiration catheter through the introducer sheath, such that the introducer sheath applies an external force to the plurality of arms to straighten the arms, and deploying plurality of arms from the introducer sheath, such that the external force is released from the plurality of arms, thereby allowing the arms to expand outward. In an alternative method, an actuation wire may be affixed to a distal hub of the infusion/aspiration catheter. The method may further comprise displacing the actuation wire distally relative to the infusion/aspiration catheter to straighten the arms while introducing the infusion/aspiration catheter into the anatomical cavity, and displacing the actuation wire proximally relative to the infusion/aspiration catheter to expand the arms outward within the anatomical cavity. In still another embodiment of the method, the elongate catheter body may further have a central lumen extending between the proximal end and distal end of the elongate catheter body, in which case, introducing the infusion/aspiration catheter into the anatomical cavity may comprise disposing a rigid stylet within the central lumen of the elongate catheter body.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description or limitation of the scope of the disclosed inventions, which is defined only by the appended claims and their equivalents. In addition, an illustrated embodiments of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects of the disclosed inventions are obtained, a more particular description of the disclosed inventions briefly described above will be rendered by reference to specific embodiments thereof, which are illustrated in the accompanying drawings. Understanding that these drawings depict only typical embodiments of the invention and are not therefore to be considered limiting of its scope, and the disclosed inventions are described and explained with additional specificity and detail through the use of the accompanying drawings, in which:

FIG. 1 is a prior art computed tomography (CT) scan slice of a normal brain;

FIG. 2 is a prior art CT scan slice of a brain that has suffered an intracerebral hemorrhage (ICH);

FIG. 3 is a plan view illustrating the introduction of a prior art external ventricular drain (EVD) catheter within a ventricle of brain that has suffered an ICH;

FIG. 4 is a plan view illustrating the infusion of recombinant tissue plasminogen activator (rt-PA) into the ventricle via the EVD catheter of FIG. 3 to treat the ICH;

FIG. 5 is a plan view illustrating the draining or aspiration of fluid including the rt-PA from the ventricle via the EVD catheter of FIG. 3 to treat the ICH;

DETAILED DESCRIPTION OF THE ILLUSTRATED EMBODIMENTS

Figure 6:
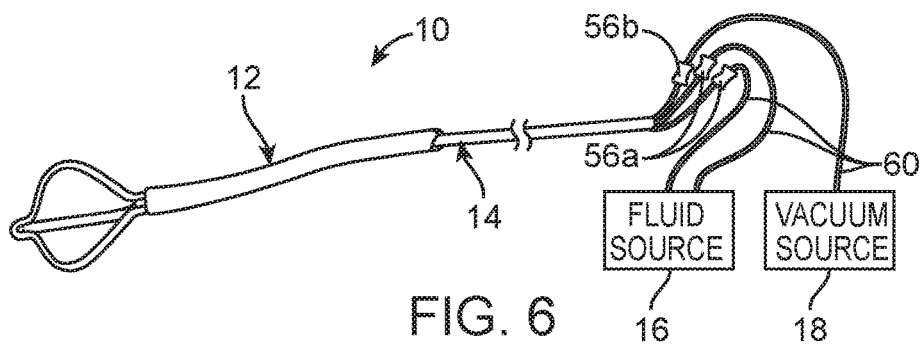
FIG. 6 is a plan view of one embodiment of an infusion/aspiration system constructed in accordance with the disclosed invention.

Referring first to FIG. 6, an infusion/aspiration system 10 constructed in accordance with one embodiment of the disclosed inventions will now be described. The infusion/aspiration system 10 generally comprises an introducer sheath 12 (which could be the primary access channel and placed separately prior to introduction of subsequent devices, or could be just a transfer sheath used to transfer other devices into a previously placed ancillary sheath), an infusion/aspiration catheter 14, a fluid source 16, and a vacuum source 18.

As best shown in FIGS. 7A-7D, the introducer sheath 12 generally comprises an elongated sheath body 20 having a proximal end 22, a distal end 24, and a lumen 26 extending therebetween. As will be described in further detail below, the infusion/aspiration catheter 14 is a purpose-built catheter that functions similarly to a conventional external ventricular drain (EVD) catheter, but has two major differences: (1) it can be delivered through the lumen 26 of the introducer sheath 12 (in the same manner as an EVD catheter) and deployed out the distal end 24 of the elongated sheath body 20 into an anatomical cavity (or clot mass) of interest, but has multiple lumens to allow simultaneous (or staged) infusion of the anatomical cavity of interest with a fluid (e.g., to dissolve a clot with recombinant tissue plasminogen activator (rt-PA)) and aspiration of the fluid, including the dissolved clot, from the anatomical cavity of interest; and (2) the distal portion of the infusion/aspiration catheter 14 expands within the anatomical cavity of interest to better distribute the infusion/aspiration functions via multiple fluid ports. Thus, the infusion/aspiration catheter 14 allows for a greater volume of clot to be treated with less diffusion resistance, thereby improving the rate of action of the procedure.

To this end, the infusion/aspiration catheter 14 generally comprises an elongate catheter body 28 having a proximal end 30 and a distal end 32. The elongate catheter body 28 is preferably sized to be introduced into a patient in a minimally invasive manner, e.g., through a burr hole (less than one-half inch in diameter) in the cranium of a patient. The elongate catheter body 28 may be composed of suitable biocompatible metals, metal alloys, polymers, metal-polymer composites, and the like, or any other suitable biocompatible material. The infusion/aspiration catheter 14 further comprises a plurality of lumens 34 extending through the elongate catheter body 28 between the proximal end 30 and the distal end 32. In the illustrated embodiment, the lumens 34 are independent of each other. That is, the lumens 34 are not in fluid communication with each other at any point. As will be described in further detail below, each lumen 34 may be arbitrarily selected to infuse or aspirate fluid. For the purposes of this specification, "aspirate" or "aspiration" means that fluid flows from a higher pressure region to a lower pressure region. However, for the purposes of illustration, the lumens 34 are shown divided between a set of infusion lumens 34a and a set of aspiration lumens 34b.

In the illustrated embodiment, the set of infusion lumens 34a comprises two infusion lumens 34a, and the set of aspiration lumens 34b comprises a single infusion lumen 34b. In alternative embodiments, the set of infusion lumens 34a may comprise a single infusion lumen 34a, and the set of aspiration lumens 34b comprises two infusion lumens 34b. In other alternative embodiments where the number of lumens 34 within the elongate catheter body 28 is greater than three, the set of infusion lumens 34a may comprise a plural number of infusion lumens 34a, and the set of aspiration lumens 34b may likewise comprise a plural number of aspiration lumens 34b, or where the number of lumens 34 within the elongate catheter body 28 is equal to two, the set of infusion lumens 34a may comprise a single infusion lumen 34a, and the set of aspiration lumens 34b may likewise comprise a single aspiration lumen 34b, as further described below with respect to FIG. 11.

The infusion/aspiration catheter 14 further comprises a plurality of arms 36 respectively having proximal ends affixed together at the distal end 32 of the elongate catheter body 28, and distal ends affixed together at a distal hub 42. The arms 36 may form a unibody structure with the elongate catheter body 28, and thus, may be composed of the same material. In the illustrated embodiment, each of the arms 36 has a lumen 44 (shown in FIG. 7D) in fluid communication with a respective one of the lumens 34 of the elongate catheter body 28, such that is a one-to-one correspondence between the lumens 34 of the elongate catheter body 28 and the arms 36, i.e., each lumen 34 of the elongated catheter body 28 is dedicated to a respective one of the arms 36. Thus, as with the lumens 44 in the elongate catheter body 28, each arm 36 can be arbitrarily selected to perform a fluid infusion, aspiration, or draining function.

In alternative embodiments, the number of arms 36 may not equal the number of lumens 34 of the elongate catheter body 28, in which case, there may not be a one-to-one correspondence between the between the lumens 34 of the elongate catheter body 28 and the arms 36. For example, a single lumen 34 of the elongated catheter body 28 can be in fluid communication with more than one lumen 44 of the respective arms 36, or multiple lumens 34 of the elongate catheter body 28 may be in fluid communication with a single lumen 44 of a respective arm 36. It is only important that the set of infusion lumens 34a and the set of aspiration lumens 34b of the elongated catheter body 28 be independent of each other, such that simultaneous infusion and aspiration of fluid through the infusion/aspiration catheter 14 can occur, as described in further detail below.

Each of the arms 36 further has at least one fluid port 46 in fluid communication with the lumen 44 of the respective arm 36. In the illustrated embodiment, each of the arms 36 comprise a plurality of fluid ports 46 extending along both the outwardly facing side and the inwardly facing side of the respective arm 36. This can be accomplished by perforating the entire thickness of the arm 36 to create two sets of aligned fluid ports 46 respectively extending along the opposite sides of the arm 36. Alternatively, the fluid ports 46 extending along the outwardly facing side and inwardly facing side of each respective arm 36 may be offset from each other along the length of the respective arm 36.

In the infusion/aspiration catheter 14 illustrated in FIG. 6, the number of arms 36 equals three, and are equi-distantly spaced from each other in a circumferential manner (in this case, spaced 120 degrees from each other), so that the entire anatomical cavity may be equally infused with fluid, although in alternative embodiments, the arms 36 may not be equi-distantly spaced from each other, e.g., to infuse fluid in a particular region or regions of the anatomical cavity in a more focused manner. Although in the infusion/aspiration catheter 14 illustrated in FIG. 6, the number of arms 36 equals three, it should be appreciated that arms 36 can have any plural number, including two, as further described below with respect to FIG. 11.

Figure 7A:
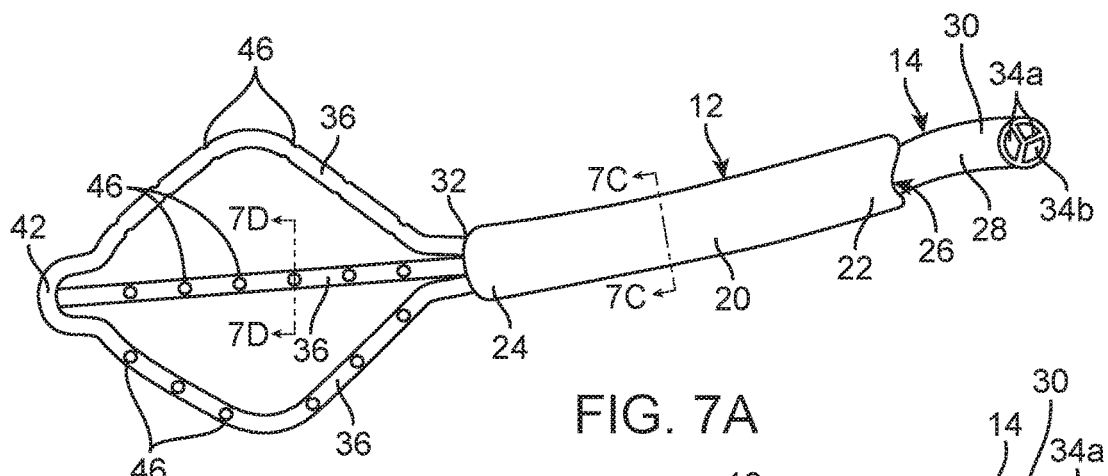
FIG. 7A is a perspective view of an infusion/aspiration catheter used in the infusion/aspiration system of FIG. 6, particularly showing the arms of the infusion/aspiration catheter in an expanded geometry.
Figure 7B:
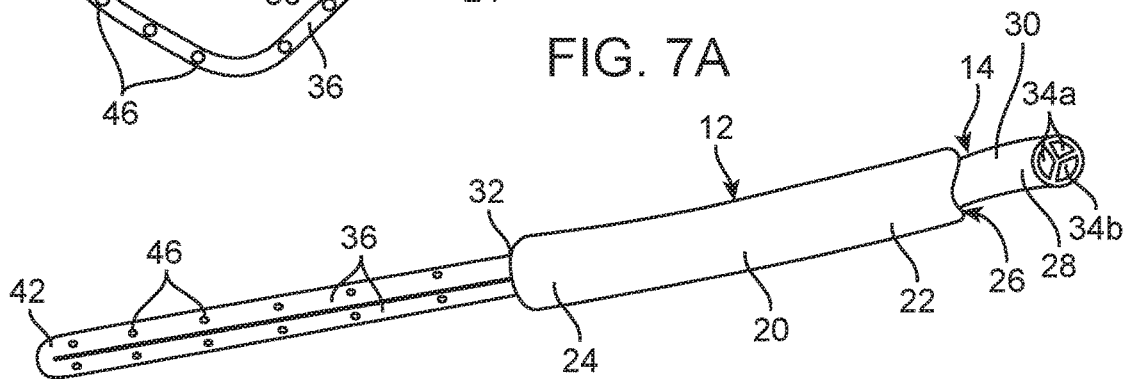
FIG. 7B is a perspective view of the infusion/aspiration catheter of FIG. 7A, particularly showing the arms of the infusion/aspiration catheter in a low-profile geometry.
Figure 7C:
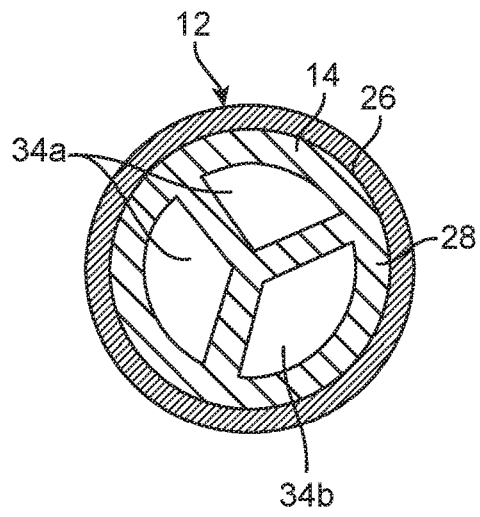
FIG. 7C is a cross-sectional view of the elongate catheter body of the infusion/aspiration catheter of FIG. 7A, taken along the line 7C-7C.
Figure 7D:
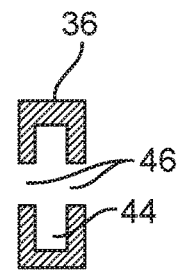
FIG. 7D is a cross-sectional view of an arm of the infusion/aspiration catheter of FIG. 7A, taken along the line 7D-7D.

The arms 36 of the infusion/aspiration catheter 14 are pre-shaped to expand outward in the absence of an external force. For example, each of the arms 36 may be a shaped element or may comprise an embedded shape memory/super-elastic forming element. Thus, as will be described in further detail below, when the infusion/aspiration catheter 14 is introduced through the lumen 26 of the introducer sheath 12, the arms 36 will be compressed by the inward external force exerted by the elongated sheath body 20 onto the arms 36, such that the arms 36 are straightened into a low-profile geometry, as best illustrated in FIG. 7B. In contrast, when the arms 36 are deployed out the distal end 24 of the elongated sheath body 20, the arms 36 will outwardly expand in the absence of the external force, thereby placing the arms 36 in an expanded geometry to fill the anatomical cavity, as best illustrated in FIG. 7A.

Figure 8:
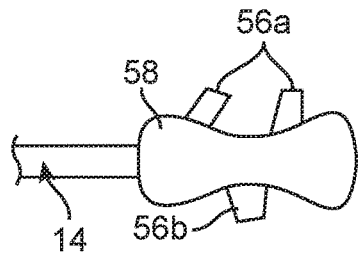
FIG. 8 is a plan view of a valve manifold that can alternatively be used in the infusion/aspiration system of FIG. 6.

Referring back to FIG. 6, the infusion/aspiration catheter 14 further comprises connectors 56 (e.g., luer connectors) affixed to the proximal end 30 of the elongate catheter body 28 in fluid communication with the lumens 34 of the elongate catheter body 28. In this embodiment, the connectors 56 are separate and free-floating, although in alternative embodiments, the infusion/aspiration catheter 14 may comprise a unitary manifold (or handle) 58 comprising the connectors 56, as illustrated in FIG. 8. Irrespective of whether the connectors 56 are free-floating or integrated into a manifold 58, in the illustrated embodiment, the number of connectors 56 equals the number of lumens 34 of the elongated catheter body 28 (three, in the embodiment illustrated in FIG. 6), and are thus, fluidly coupled to the lumens 34 in a dedicated manner. Optionally, a valved switched manifold may be used as well, in which case, the lumens 34 of the elongate catheter body 28 may be switched to either the aspiration or infusion manifold, and therefore, only two connectors 56 are needed.

In the illustrated embodiment, the connectors 56 are divided between two infusion connectors 56a, which corresponds to the two infusion lumens 34a, and a single aspiration connector 56b, which corresponds to the single aspiration lumen 34b. That is, the two infusion connectors 56a are respectively in fluid communication with the two infusion lumens 34a of the elongate catheter body 28, and the aspiration connector 56b is in fluid communication with the aspiration lumen 34b of the elongate catheter body 28. Of course, in the alternative embodiment where two of the lumens 34 are aspiration lumens 34b, and the remaining lumen 34 is a single infusion lumen 34a, a single infusion connector 56a may be in fluid communication with the single infusion lumen 34a, and two aspiration connectors 56b may be respectively in fluid communication with the two aspiration lumens 34b.

The fluid source 16 may, e.g., take the form of a standard hospital saline bag, and the vacuum source 18 may take the form of a vacuum bottle, a syringe, a vacuum pump, or other suitable type of vacuum source. For the purposes of this specification, "vacuum" means a region of lower pressure relative to an inlet pressure. A conventional fluid control system (not shown), including a pump and valves, may be used to control the flow of fluid from the fluid source 16 into the infusion/aspiration catheter 14, and the flow of fluid from the infusion/aspiration catheter 14 into the vacuum source 18. Exemplary fluid control systems are described in U.S. patent application Ser. No. 15/480,354, which is expressly incorporated herein by reference. The fluid source 16 is connected to the two infusion connectors 56a respectively leading to the two infusion lumens 34a within the elongate catheter body 28, whereas the vacuum source 18 is connected to the aspiration connector 56b leading to the aspiration lumen 34b within the elongate catheter body 28. Thus, the fluid source 16 is fluidly coupled to the lumens 44, and thus the fluid ports 46, of two of the arms 36, whereas the vacuum source 18 is fluidly coupled to the lumen 44, and thus the fluid ports 46, of the remaining arm 36. Extension tubing 60 may optionally be used to couple the fluid source 16 and vacuum source 18 to the respective infusion connectors 56a and aspiration connectors 56b.

It should be appreciated that, although the number of connectors 56 have been described as being equal to the number of lumens 34 of the elongate catheter body 28, such that the connectors 56 can be in respective fluid communication with these lumens 34 in a dedicated manner, the number of connectors 56 may alternatively be less than the number of lumens 34 of the elongate catheter body 28. For example, a single infusion connector 56a can be in fluid communication with the two infusion lumens 34a of the elongate catheter body 28, and a single aspiration connector 56b can be in fluid communication with the aspiration lumen 34b of the elongate catheter body 28.

It should also be appreciated that the designation of any particular connector 56 as an infusion connector 56a or an aspiration connector 56b, and thus the designation of any particular lumen (or lumens) 34 of the elongate catheter body 28 as either an infusion lumen (or lumens) 34a or an aspiration lumen (or lumens) 34b, may be arbitrary in that it depends on whether the fluid source 16 or the aspiration pump 18 is connected to that particular connector 56. That is, if the fluid source 16 is connected to a particular connector 56, that connector 56 will be an infusion connector 56a, and the lumen (or lumens) 34 of the elongate catheter body 28 in fluid communication with that connector 56a will be an infusion lumen (or lumens) 34a. Likewise, if the vacuum source 18 is connected to a particular connector 56, that connector 56 will be an aspiration connector 56b, and the lumen (or lumens) 34 of the elongate catheter body 28 in fluid communication with that connector 56b will be an aspiration lumen (or lumens) 34b.

It should also be appreciated that, by not connecting the fluid source 16 or the vacuum source 18 to any of the particular connectors 56, each of these connectors 56 can function as a drainage connector, and thus, any of the lumen (or lumens) 34 of the elongated catheter body 28 in fluid communication with that connector 56 can function as a drainage lumen. As such, the infusion/aspiration catheter 14, at any particular time, can also serve as a drainage catheter, with the expanded arms 36 associated with such drainage lumen(s) 34 advantageously providing more drainage locations, in addition to more infusion and aspiration locations for the infusion/aspiration functions.

Figures 9, 13:
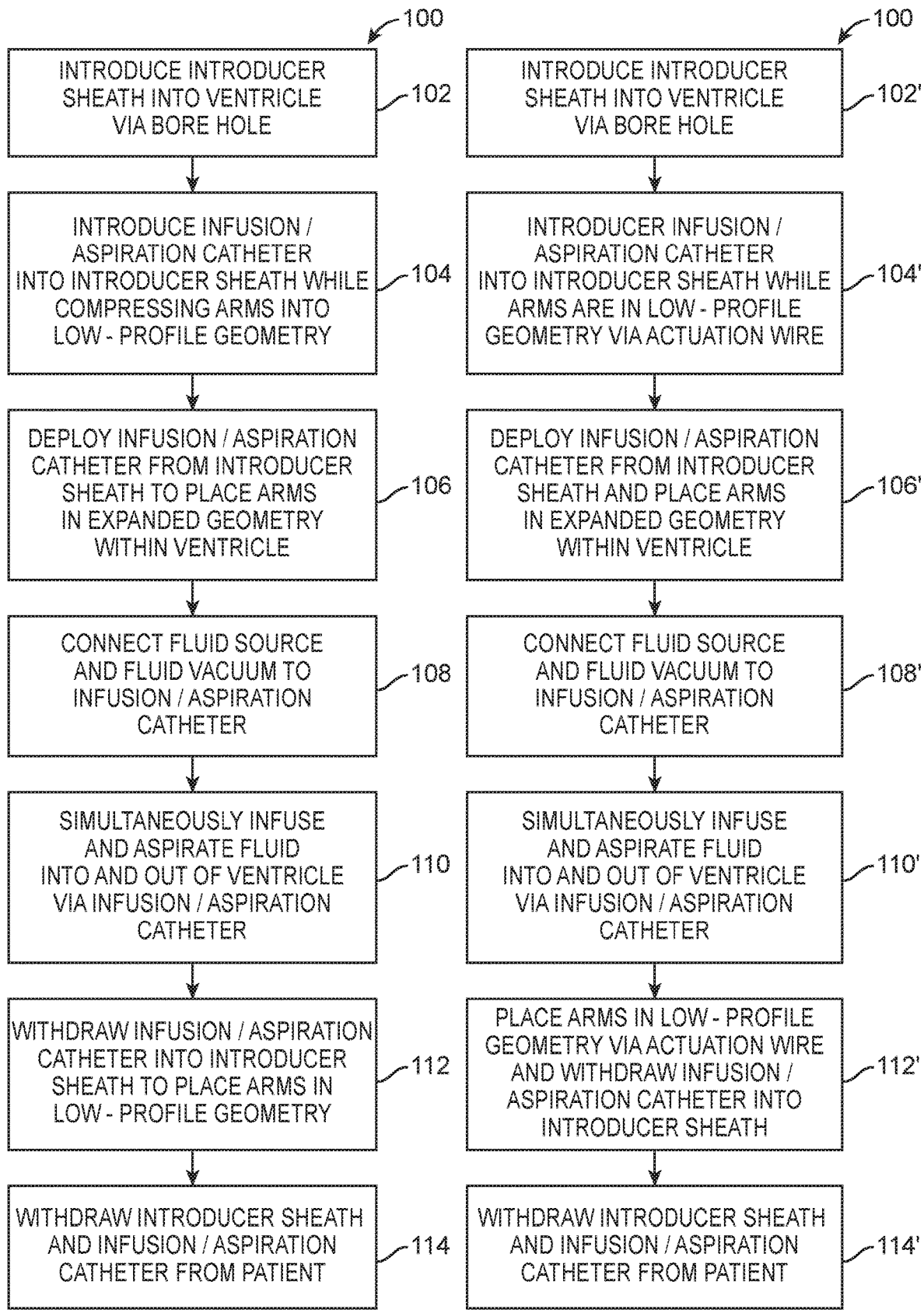
FIG. 9 is a flow diagram illustrating one method of using the infusion/aspiration system of FIG. 6 to treat an ICH within a brain of a patient.
FIG. 13 is a flow diagram illustrating one method of using the infusion/aspiration system of FIG. 11 to treat an ICH within a brain of a patient

Having described the structure and operation of the infusion/aspiration system 10, one method 100 of operating it to treat an anatomical cavity 82 of a patient will now be described with respect to FIG. 9, as well as FIGS. 10A-10D. In this exemplary method, the anatomical cavity 82 is a ventricle within the cranium 84 of the patient, and the patient 80 has suffered a hemorrhagic stroke of the brain 80 (i.e., an ICH), resulting in a clot 86 within the ventricle 82, such that the treatment of the patient involves infusing fluid comprising rt-PA into the ventricle 82 to dissolve the clot 86, and the rt-PA fluid, along with the dissolved clot 86, is aspirated out from the ventricle 82.

Figure 10A:
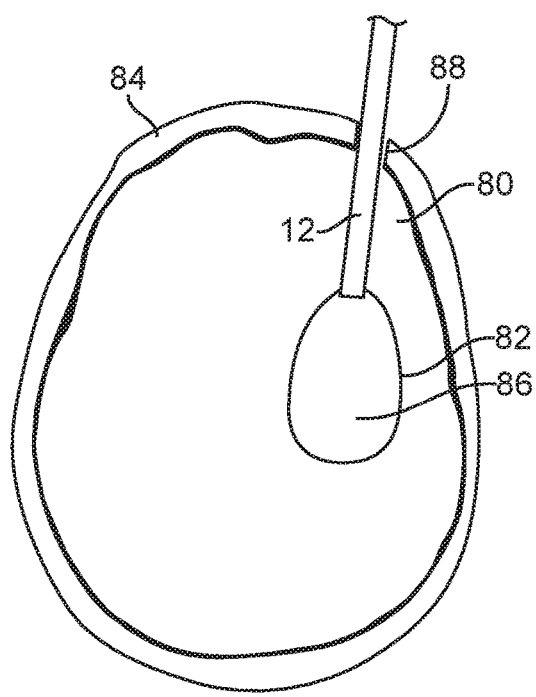
FIGS. 10A-10D are plan views illustrating the use of the infusion/aspiration system of FIG. 6 to treat the ICH within the brain of the patient in accordance with the method of FIG. 9.
Figure 10B:
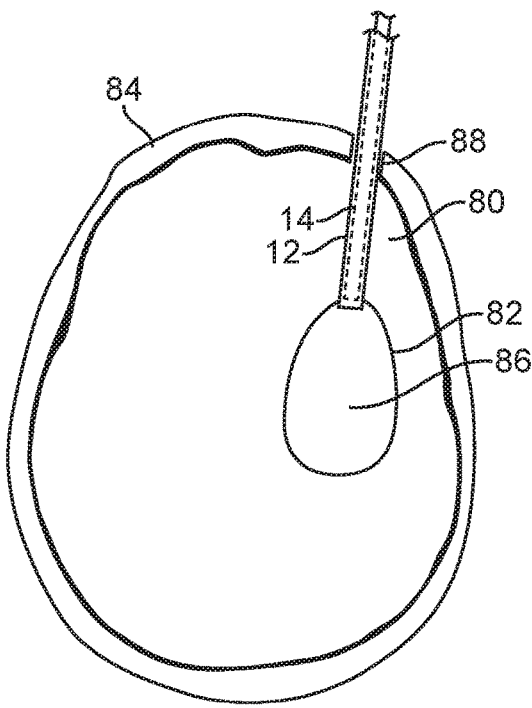

To this end, the method 100 comprises introducing the introducer sheath 12 into the ventricle 82 via a bore hole 88 conventionally formed through the cranium 84 (step 102) (see FIG. 10A). The introducer sheath 12 may be tracked over an image-guide access probe along a pre-determined non-linear path to minimize potential damage to eloquent tissue. Next, the infusion/aspiration catheter 14 is introduced into the lumen 26 of the introducer sheath 12, such that the introducer sheath 12 applies an external force to the arms 36 of the infusion/aspiration catheter 14 (shown partially in phantom), thereby straightening the arms 36 out into a low-profile geometry (step 104) (see FIG. 10B).

Figure 10C:
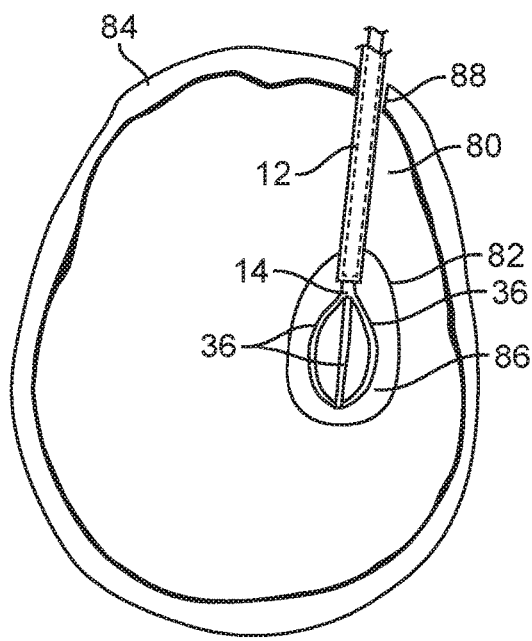

Next, the arms 36 of the infusion/aspiration catheter 14 are deployed from the distal end 24 of the introducer sheath 12 into the ventricle 82, such that the external force is released from the arms 36, thereby allowing the arms 12 to expand outward into an expanded geometry (step 106) (see FIG. 10C). This can be accomplished by, e.g., pushing the infusion/aspiration catheter 14 in the distal direction while maintaining the same position of the introducer sheath 12, or pulling the introducer sheath 12 in the proximal direction while maintaining the same position of the infusion/aspiration catheter 14. Next, the fluid source 16 and the vacuum source 18 are connected to the respective infusion connector(s) 56a and aspiration connector(s) 56b of the infusion/aspiration catheter 14 (step 108). Although this step is illustrated as occurring after deployment of the arms 36 into the ventricle 82, this step can occur any time prior to the infusion/aspiration process, including prior to introduction of the introducer sheath 12 into the ventricle 82.

Figure 10D:
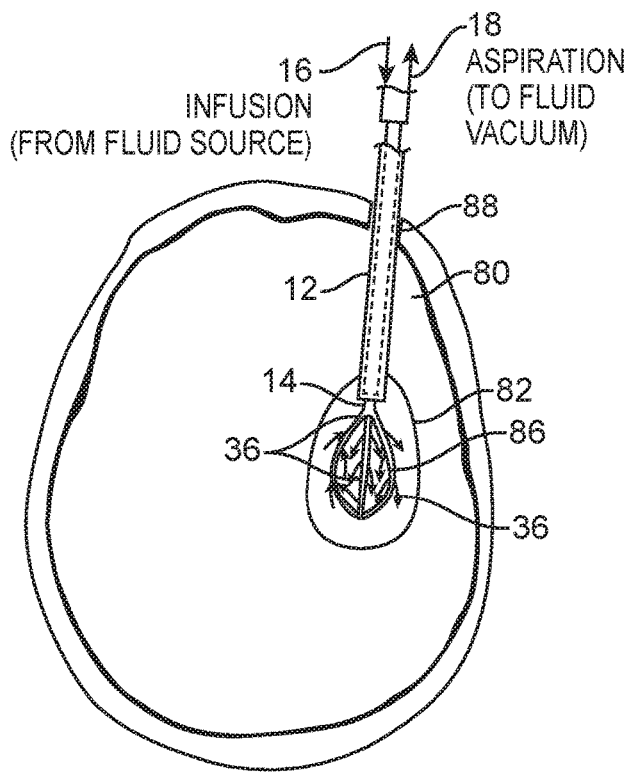

Fluid comprising rt-PA is then simultaneously infused into and aspirated from the ventricle 82 (step 110) (see FIG. 10D). That is, rt-PA fluid will flow from the fluid source 16 into the infusion connector(s) 56a, through the two infusion lumens 34a within the elongate catheter body 28, through the lumens 44, and out the fluid ports 46, of two of the arms 36, thereby dissolving the clot 86, and simultaneously, the rt-PA fluid and any dissolved clot 86, will flow into the fluid ports 46, and through the lumen 44, of the remaining arm 36, through the aspiration lumen 34b within the elongate catheter body 28, out of the aspiration connector(s) 56b, and into the vacuum source 18. Alternatively, other forms of treatment, which may include or not include the administration of rt-PA, may be administered via the lumens 44 of the elongated catheter body 28. Such alternative treatments can, e.g., include saline lavage, which removes unwanted potentially toxic substances, which may arise due to the presence of the clot, and could be the primary cause of tissue damage; introduction of hyperosmotic solution to help reduce local edema; introduction of some unknown therapeutic agent that "fixes brain," etc.

The method 100 may optionally comprise draining the fluid by disconnecting one or both of the fluid source 16 and aspiration pump 18 from one or more of the connectors 56. That is, fluid will drain into the fluid ports 46, and through the lumen(s) 44, of the arm(s) 36, through the lumen(s) 34 within the elongate catheter body 28, out of the connector(s) 56, and into a basin under atmospheric pressure. Optionally, an automated system may be used to infuse, aspirate, and/or drain according to a predetermined schedule or in response to a measured input, such as the patient intracranial pressure (ICP) or the static pressure measured from the catheter body 28 (which may be a direct measure of the ICP).

After the procedure is completed (i.e., the clot 86 has been completely (or sufficiently) evacuated from the ventricle 82), the arms 36 of the infusion/aspiration catheter 14 can be proximally withdrawn into the introducer sheath 12 or the introducer sheath 12 can be distally displaced to re-sheath the arms 36, such that the introducer sheath 12 again applies an external force to the arms 36 of the infusion/aspiration catheter 14, thereby straightening the arms 36 back out into a low-profile geometry (step 112). The introducer sheath 12, along with the infusion/aspiration catheter 14, can then be removed from the patient (step 114).

Figure 11:
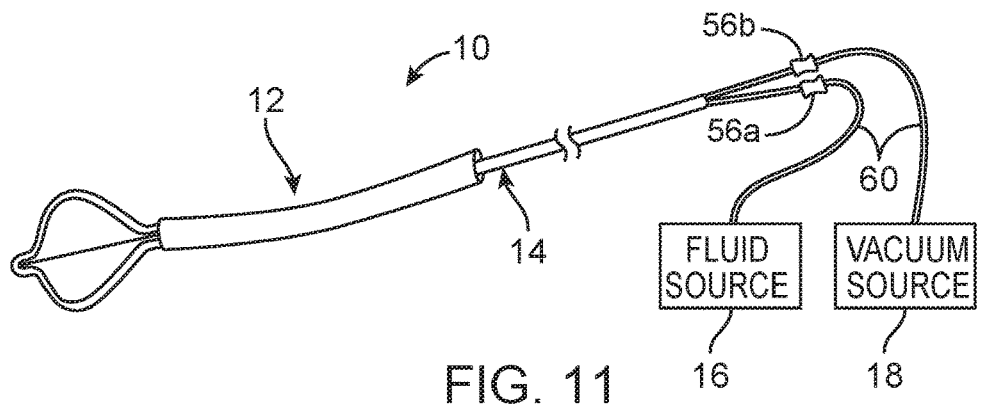
FIG. 11 is a plan view of another embodiment of an infusion/aspiration system constructed in accordance with the disclosed invention.
Figure 12A:
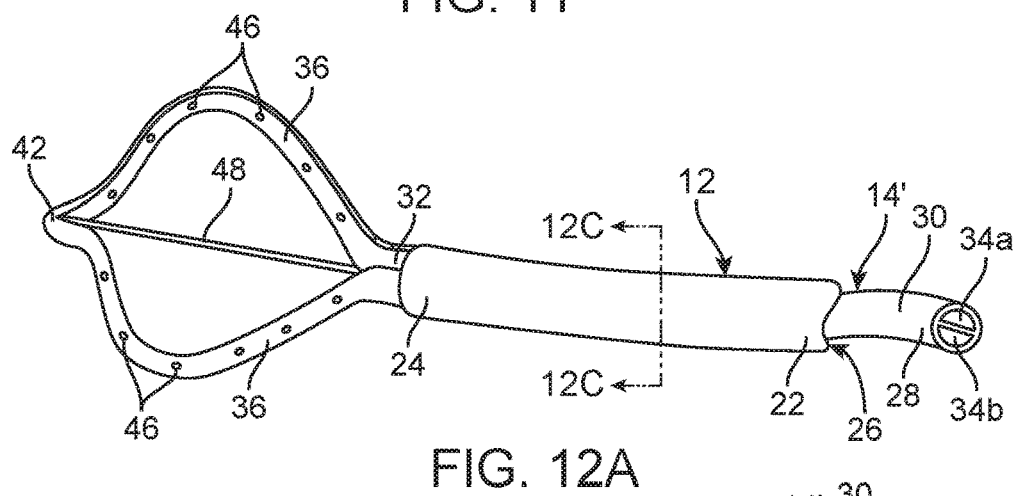
FIG. 12A is a perspective view of an infusion/aspiration catheter used in the infusion/aspiration system of FIG. 11, particularly showing the arms of the infusion/aspiration catheter in an expanded geometry.
Figure 12B:
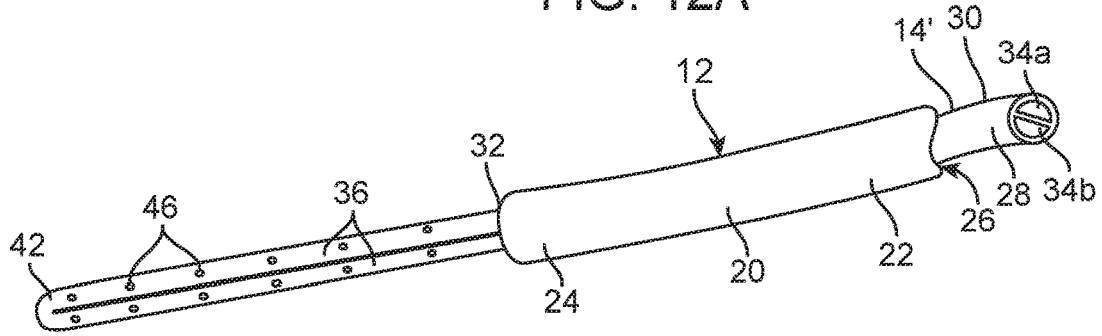
FIG. 12B is a perspective view of the infusion/aspiration catheter of FIG. 12A, particularly showing the arms of the infusion/aspiration catheter in a low-profile geometry.
Figure 12C:
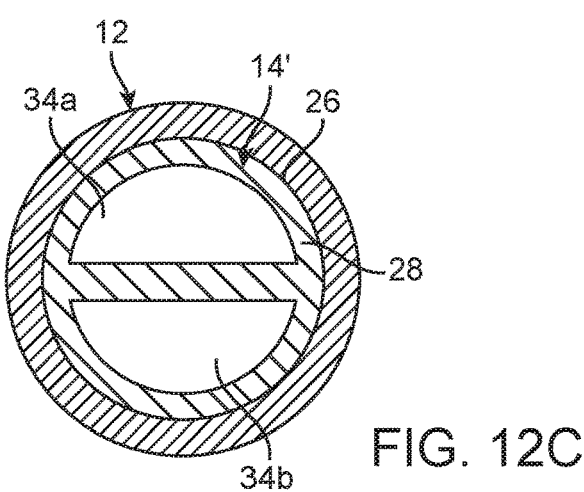
FIG. 12C is a cross-sectional view of the elongate catheter body of the infusion/aspiration catheter of FIG. 12A, taken along the line 12C-12C

Referring now to FIG. 11, an infusion/aspiration system 10' constructed in accordance with another embodiment of the disclosed inventions will now be described. As best shown in FIGS. 12A-12C, the infusion/aspiration system 10' is similar to the infusion/aspiration system 10 illustrated in FIG. 6, with the exception that it comprises an infusion/aspiration catheter 14' that comprises only two arms 36. In this embodiment, the two arms 36 are circumferentially spaced from each other by one hundred eighty degrees, although the two arms 36 may be spaced from each other at an angle different from one hundred eight degrees, e.g., to focus infusion of the fluid in only one region of the anatomical cavity.

In this embodiment, the set of infusion lumens 34a comprises a single infusion lumen 34a, and the set of aspiration lumens 34b likewise comprises a single infusion lumen 34b. In the illustrated embodiment, the lumen 44 of each of the arms 36 in fluid communication with a respective one of the lumens 34 of the elongate catheter body 28, such that is a one-to-one correspondence between the lumens 34 of the elongate catheter body 28 and the arms 36, i.e., each lumen 34 of the elongated catheter body 28 is dedicated to a respective one of the arms 36.

In alternative embodiments, the number of arms 36 may not equal the number of lumens 34 of the elongate catheter body 28, in which case, there may not be a one-to-one correspondence between the between the lumens 34 of the elongate catheter body 28 and the arms 36. For example, multiple lumens 34 of the elongate catheter body 28 may be in fluid communication with a single lumen 44 of a respective arm 36. Again, it is only important that the set of infusion lumens 34a and the set of aspiration lumens 34b of the elongated catheter body 28 be independent of each other, such that simultaneous infusion and aspiration of fluid through the infusion/aspiration catheter 14 can occur, as described in further detail below.

A single infusion connector 56a and a single aspiration connector 56b are affixed to the proximal end 30 of the elongate catheter body 28 in fluid communication with the respective infusion lumen 34a and aspiration lumen 34b of the elongate catheter body 28. In the embodiment illustrated in FIG. 11, the connectors 56 are separate and free-floating, although in alternative embodiments, the infusion/aspiration catheter 14' may comprise a unitary manifold (similar to the manifold 58 illustrated in FIG. 8) comprising the connectors 56. Irrespective of whether the connectors 56 are free-floating or integrated into a manifold, the fluid source 16 is connected to the infusion connector 56a leading to the infusion lumen 34a within the elongate catheter body 28, whereas the vacuum source 18 is connected to the aspiration connector 56b leading to the aspiration lumen 34b within the elongate catheter body 28. Thus, the fluid source 16 is fluidly coupled to the lumens 44, and thus the fluid ports 46, of one arm 36, whereas the vacuum source 18 is fluidly coupled to the lumen 44, and thus the fluid ports 46, of the remaining arm 36.

In the infusion/aspiration catheter 14' illustrated in FIG. 11, instead of, or in addition to, pre-shaping the arms 36 to expand outward in the absence of an external force, the infusion/aspiration catheter 14' further comprises an actuation wire 48 slidably disposed within an additional lumen (not shown) within the elongated catheter body 28, as best shown in FIGS. 12A-12C. The actuation wire 48 (best shown in FIG. 12A) has a distal end affixed to the distal hub 42 of the elongated catheter body 28 and a proximal end extending out of the proximal end 30 of the elongated catheter body 28 for manipulation by a physician to alternately place the arms 36 between a low-profile geometry and an expanded geometry. That is, by proximally displacing the actuation wire 48 within the lumen (not shown) relative to the elongate catheter body 28, the arms 36 will expand outward into the expanded geometry (see FIG. 12A), and by distally displacing the actuation wire 48 within the lumen relative to the elongate catheter body 28, the arms 36 will straighten back out into the low-profile geometry (see FIG. 12B).

Having described the structure and operation of the infusion/aspiration system 10', another method 100' of operating it to treat the anatomical cavity 82 of a patient 80 will now be described with respect to FIG. 13, as well as FIGS. 14A-14D. As with the previous exemplary method 100, in this method 100', the anatomical cavity 82 is a ventricle within the cranium 84 of the patient 80, and the patient 80 has suffered a hemorrhagic stroke, resulting in a clot 86 within the ventricle 82, such that the treatment of the patient 80 involves infusing fluid comprising rt-PA, into the ventricle 82 to dissolve the clot 86, and the rt-PA fluid, along with the dissolved clot 86, is aspirated out from the ventricle 82.

Figure 14A:
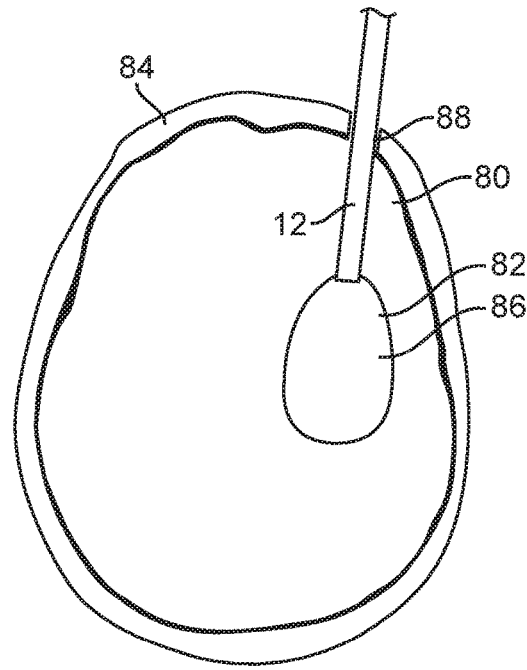
FIGS. 14A-14D are plan views illustrating the use of the infusion/aspiration system of FIG. 11 to treat the ICH within the brain of the patient in accordance with the method of FIG. 13.
Figure 14B:
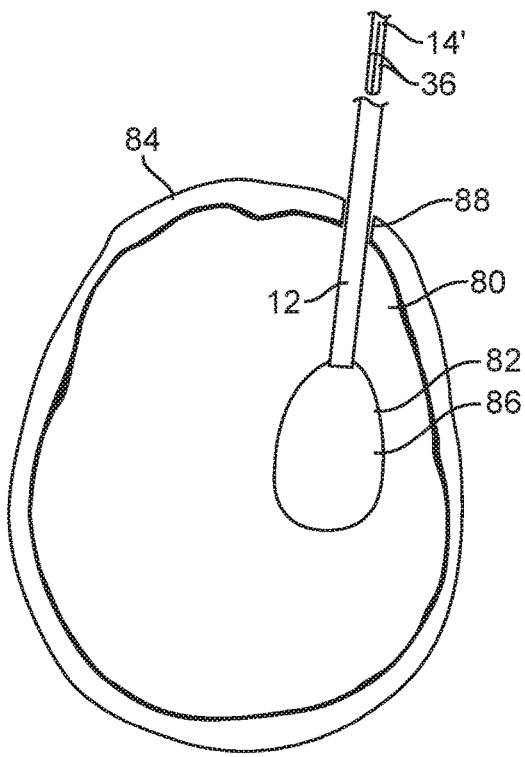
Figure 14C:
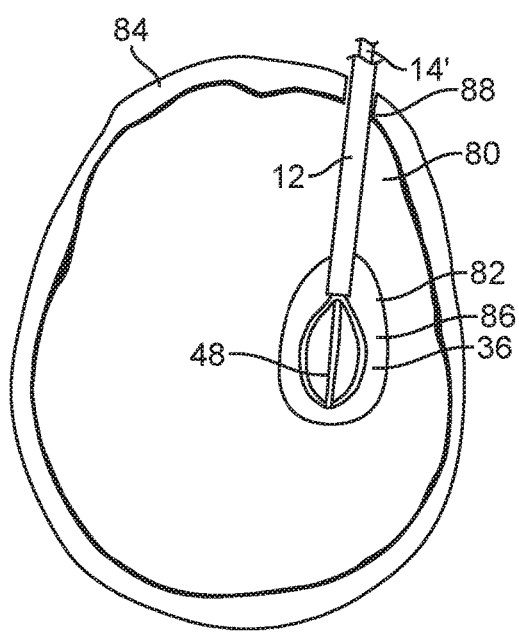

To this end, the method 100' comprises introducing the introducer sheath 12 into the ventricle 82 via a bore hole 88 conventionally formed through the cranium 84 (step 102') (see FIG. 14A). The introducer sheath 12 may be tracked over an image-guide access probe along a pre-determined non-linear path to minimize potential damage to eloquent tissue. Next, the infusion/aspiration catheter 14 is introduced into the lumen 26 of the introducer sheath 12, while the actuation wire 48 is displaced distally within the additional lumen (not shown) relative to the elongate catheter body 28 to straighten the arms 36 into the low-profile geometry (step 104') (see FIG. 14B). Next, the arms 36 of the infusion/aspiration catheter 14 are deployed from the distal end 24 of the introducer sheath 12 into the ventricle 82, and the actuation wire 48 is displaced proximally within the additional lumen relative to the elongate catheter body 28 to expand the arms 36 outward into the expanded geometry (step 106') (see FIG. 14C). Next, the fluid source 16 and the vacuum source 18 are connected to the respective infusion connector 56a and aspiration connector 56b of the infusion/aspiration catheter 14 (step 108').

Figure 14D:
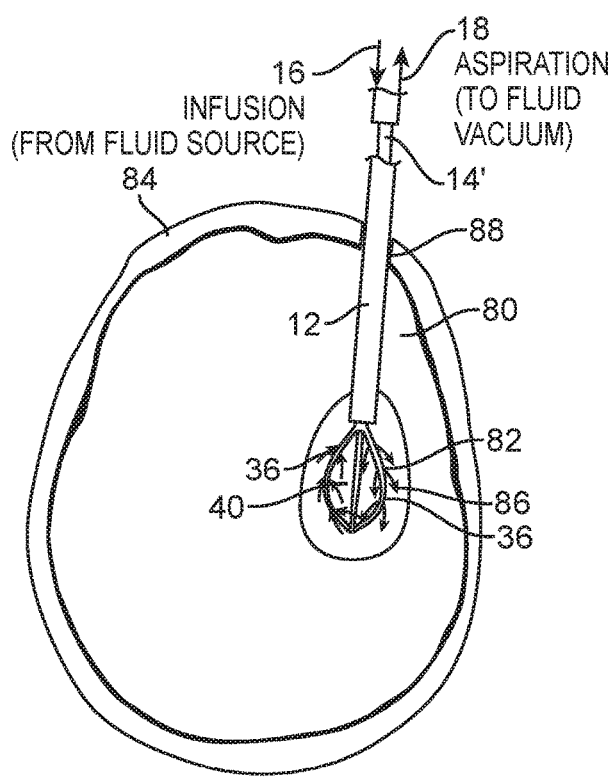

Fluid comprising rt-PA (or another therapeutic solution) is then simultaneously infused into and aspirated from the ventricle 82 (step 110) (see FIG. 14D). That is, rt-PA fluid will flow from the fluid source 16 into the infusion connector 56a, through the single infusion lumen 34a within the elongate catheter body 28, through the lumen 44, and out the fluid ports 46, of one of the arms 36, thereby dissolving the clot 86, and simultaneously, the rt-PA fluid and any dissolved clot 86, will flow into the fluid ports 46, and through the lumen 44, of the remaining arm 36, through the aspiration lumen 34b within the elongate catheter body 28, out of the aspiration connector 56, and into the vacuum source 18.

The method 100' may optionally comprise aspirating by draining the fluid by disconnecting one or both of the fluid source 16 and aspiration pump 18 from one or more of the connectors 56. That is, fluid will drain into the fluid ports 46, and through the lumen(s) 44, of the arm(s) 36, through the lumen(s) 34 within the elongate catheter body 28, out of the connector(s) 56, and into a basin under atmospheric pressure (or optionally using an automated system to infuse, aspirate, and/or drain).

After the procedure is completed, the actuation wire 48 is displaced distally within the additional lumen relative to the elongate catheter body 28 to straighten the arms 36 back out into the low-profile geometry (step 112'), and the arms 36 of the infusion/aspiration catheter 14 can be proximally withdrawn into the introducer sheath 12 or the introducer sheath 12 can be distally displaced to re-sheath the arms 36. Alternatively, the elongate catheter body 28 can be retracted directly into the introducer sheath 12, with the actuation wire 48 left free to slide distally as the elongated catheter body 28 is resheathed into the introducer sheath 12. The introducer sheath 12, along with the infusion/aspiration catheter 14, can then be removed from the patient (step 114').

Figure 15:
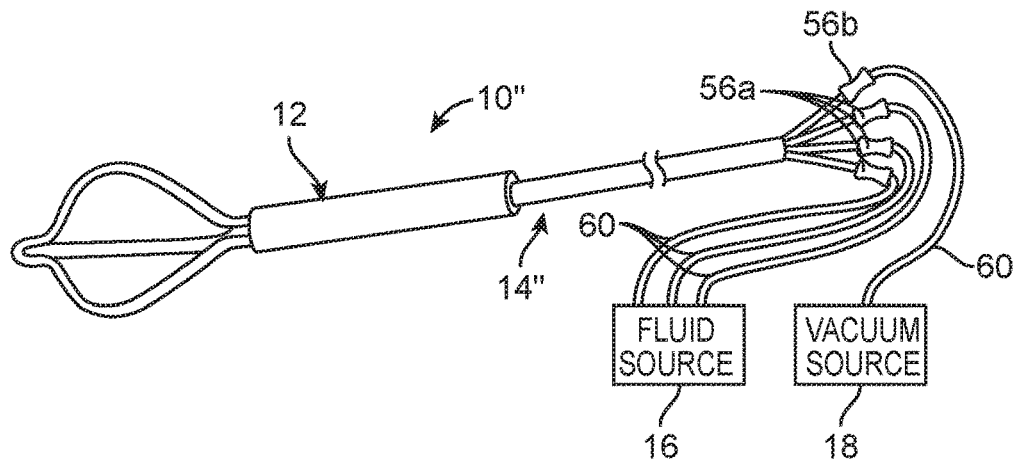
FIG. 15 is a plan view of still another embodiment of an infusion/aspiration system constructed in accordance with the disclosed invention.
Figure 16A:
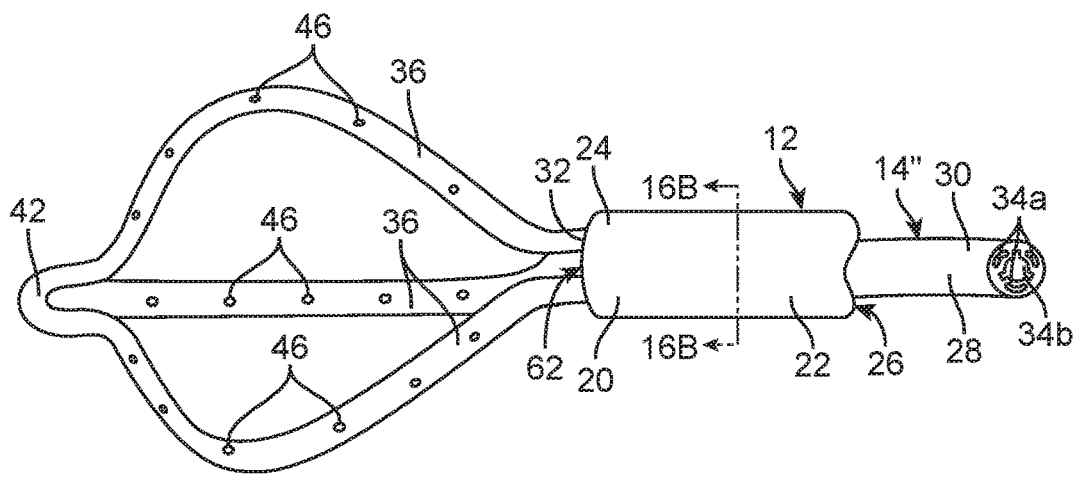
FIG. 16A is a perspective view of an infusion/aspiration catheter used in the infusion/aspiration system of FIG. 15.
Figure 16B:
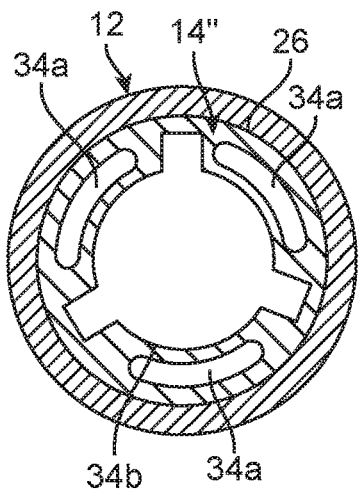
FIG. 16B is a cross-sectional view of the elongate catheter body of the infusion/aspiration catheter of FIG. 16A, taken along the line 16B-16B.

Referring now to FIG. 15, an infusion/aspiration system 10" constructed in accordance with still another embodiment of the disclosed inventions will now be described. The infusion/aspiration system 10" is similar to the infusion/aspiration system 10' illustrated in FIG. 6, with the exception that it comprises an infusion/aspiration catheter 14" that has a central aspiration lumen 34b extending through the elongated catheter body 28 between the proximal end 30 and the distal end 32, with the other three lumens 34b serving as infusion lumens that circumferentially surround the aspiration lumen 34b, as best illustrated in FIG. 16. The aspiration lumen 34b terminates in a distal fluid port 62 at the distal end 32 of the elongate catheter body 28 between the proximal ends of the arms 36. In the embodiment illustrated in FIG. 16, the central aspiration lumen 34b has a cross-sectional area greater than the cross-section area of each of the surrounding infusion lumens 34a, thereby lending itself well to aspiration.

In the same manner described above with respect to the infusion/aspiration catheter 14' in FIG. 6, the connectors 56 are affixed to the proximal end 30 of the elongate catheter body 28 in fluid communication with the lumens 34 of the elongate catheter body 28, and can be free-floating, as illustrated in FIG. 15, or may be incorporated into a unitary manifold 58 in a similar manner illustrated in FIG. 8. The number of connectors 56 equals the number of lumens 34 of the elongated catheter body 28 (four, in the embodiment illustrated in FIG. 15), and are thus, fluidly coupled to the lumens 34 in a dedicated manner. Alternatively, a single connector 56 and a single lumen 34 of the elongated catheter body 28 may be fluidly coupled to the lumens 44 of the three arms 36.

In the illustrated embodiment, the connectors 56 are divided between three infusion connectors 56a, which corresponds to the three surrounding infusion lumens 34a, and a single aspiration connector 56b, which corresponds to the single central aspiration lumen 34b. That is, the three infusion connectors 56a are respectively in fluid communication with the three infusion lumens 34a of the elongate catheter body 28, and the aspiration connector 56b is in fluid communication with the aspiration lumen 34b of the elongate catheter body 28. Of course, just as with the infusion/aspiration catheter 10 of FIG. 6, the designation of any particular connector 56 as an infusion connector 56a or an aspiration connector 56b, and thus the designation of any particular lumen (or lumens) 34 of the elongate catheter body 28 as either an infusion lumen (or lumens) 34a or an aspiration lumen (or lumens) 34b, may be arbitrary in that it depends on whether the fluid source 16 or the aspiration pump 18 is connected to that particular connector 56.

The fluid source 16 is connected to the three infusion connectors 56a respectively leading to the three infusion lumens 34a within the elongate catheter body 28 (or a single infusion connector leading to a single infusion lumen within the elongate catheter body 28), whereas the vacuum source 18 is connected to the aspiration connector 56b leading to the aspiration lumen 34b within the elongate catheter body 28. Thus, the fluid source 16 is fluidly coupled to the lumens 44, and thus the fluid ports 46, of the three arms 36, whereas the vacuum source 18 is fluidly coupled to the lumen 44, and thus the distal fluid port 62 between the proximal ends of the arms 36.

It should be appreciated that, although the number of connectors 56 have been described as being equal to the number of lumens 34 of the elongate catheter body 28, such that the connectors 56 can be in respective fluid communication with these lumens 34 in a dedicated manner, the number of connectors 56 may alternatively be less than the number of lumens 34 of the elongate catheter body 28. For example, a single infusion connector 56a can be in fluid communication with the three surrounding infusion lumens 34a of the elongate catheter body 28, and a single aspiration connector 56b can be in fluid communication with the central aspiration lumen 34b of the elongate catheter body 28.

It should also be appreciated that, just as with the embodiment illustrated in FIG. 6, the designation of any particular connector 56 as an infusion connector 56a or an aspiration connector 56b, and thus the designation of any particular lumen (or lumens) 34 of the elongate catheter body 28 as either an infusion lumen (or lumens) 34a or an aspiration lumen (or lumens) 34b, may be arbitrary in that it depends on whether the fluid source 16 or the aspiration pump 18 is connected to that particular connector 56. That is, if the fluid source 16 is connected to a particular connector 56, that connector 56 will be an infusion connector 56a, and the lumen (or lumens) 34 of the elongate catheter body 28 in fluid communication with that connector 56a will be an infusion lumen (or lumens) 34a. Likewise, if the vacuum source 18 is connected to a particular connector 56 that connector 56 will be an aspiration connector 56b, and the lumen (or lumens) 34 of the elongate catheter body 28 in fluid communication with that connector 56b will be an aspiration lumen (or lumens) 34b.

Furthermore, in an alternative embodiment, the number of lumens 34 of the elongate catheter body 28 may not match the number of lumens 44 of the arms 36. For example, it may be advantageous to have only one infusion lumen 34a that is in fluid communication with the three lumens 44 of the arms 36 via a coupling at the proximal ends or the distal ends of the arms 36. In this manner, the cross-sectional size of the aspiration lumen 34b may be maximized. Furthermore, in an optional embodiment where the aspiration lumen 34b is large enough to be capable of ingesting large clot masses, and thus, also being capable to be clogged, the infusion/catheter 10" may comprise a maceration tool (not shown), e.g., a rotary cutter/impeller, ultrasound probe, reciprocating wire, etc., that resides in the aspiration lumen 34b.

The method of operating the infusion/catheter system 10" is similar to the operation of the infusion/catheter system 10 of FIG. 6 (see FIGS. 10A-10D), with the exception that the previously infused rt-PA fluid and dissolved clot 86 will flow into the distal fluid port 62 at the distal end 32 of the elongate catheter body 28 (instead of into the fluid ports 46 of the arm(s) 36, through the central aspiration lumen 34b within the elongate catheter body 28, out of the aspiration connector 56b, and into the vacuum source 18.

Figure 17:
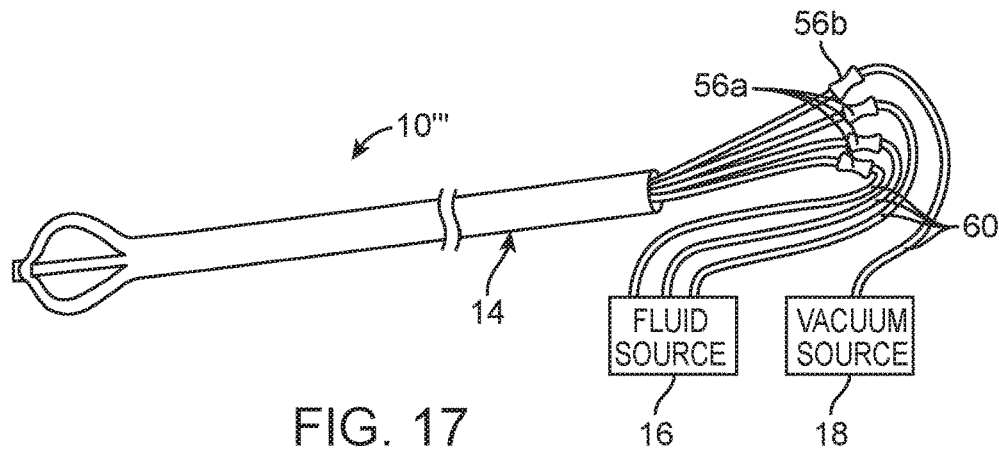
FIG. 17 is a plan view of yet another embodiment of an infusion/aspiration system constructed in accordance with the disclosed inventions.
Figure 18A:
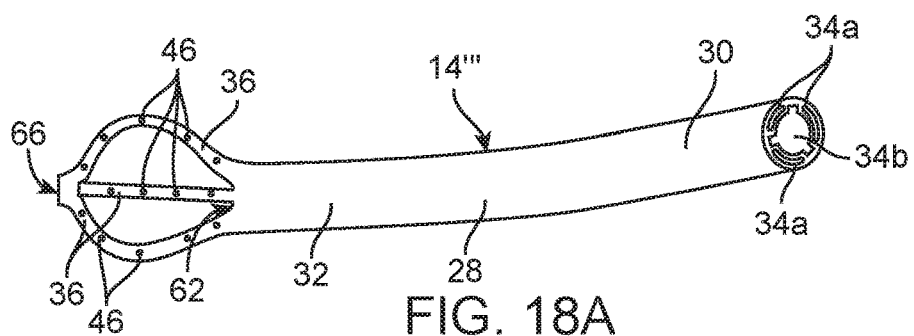
FIG. 18A is a perspective view of an infusion/aspiration catheter used in the infusion/aspiration system of FIG. 17, particularly showing the arms of the infusion/aspiration catheter in an expanded geometry.
Figure 18B:
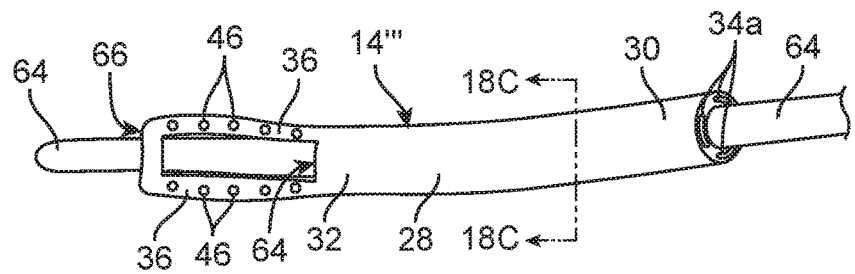
FIG. 18B is a perspective view of the infusion/aspiration catheter of FIG. 18A, particularly showing the arms of the infusion/aspiration catheter in a low-profile geometry.
Figure 18C:
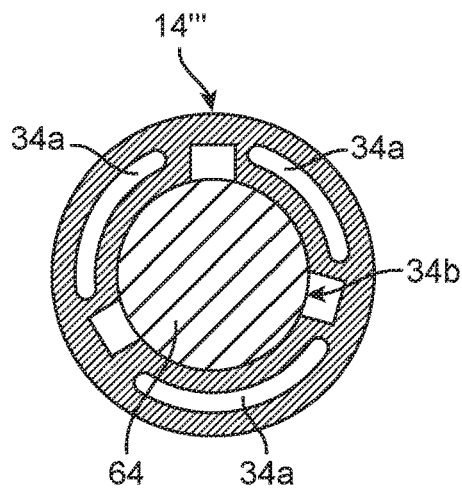
FIG. 18C is a cross-sectional view of the elongate catheter body of the infusion/aspiration catheter of FIG. 18A, taken along the line 18C-18C.

Referring now to FIG. 17, an infusion/aspiration system 10''' constructed in accordance with yet another embodiment of the disclosed inventions will now be described. The infusion/aspiration system 10''' is similar to the infusion/aspiration system 10" illustrated in FIG. 15, with the exception that the arms 36 of the infusion/aspiration catheter 14''' are made smaller to better serve as a filter to prevent, or at least minimize, aspiration of tissue into the distal fluid port 62 of the elongate catheter body 28, as best illustrated in FIG. 18. The infusion/aspiration catheter 14''' further optionally comprises a rigid stylet 64 removably disposed within the central aspiration lumen 34b of the elongate catheter body 28. The distal hub 42 of the infusion/aspiration catheter 14' comprises an aperture 66 through which the rigid stylet 64 is disposed to straighten the arms 36 out into a low-profile geometry. Thus, as it will be described in further detail below, the rigid stylet 64 may aid placement of the infusion/aspiration catheter 14" within the anatomical cavity, with or without the use of the introducer sheath 12. The rigid stylet 64 may be removed from the infusion/aspiration catheter 14''', so that the central aspiration lumen 34b may subsequently be used to aspirate fluid from the anatomical cavity.

Figure 19:
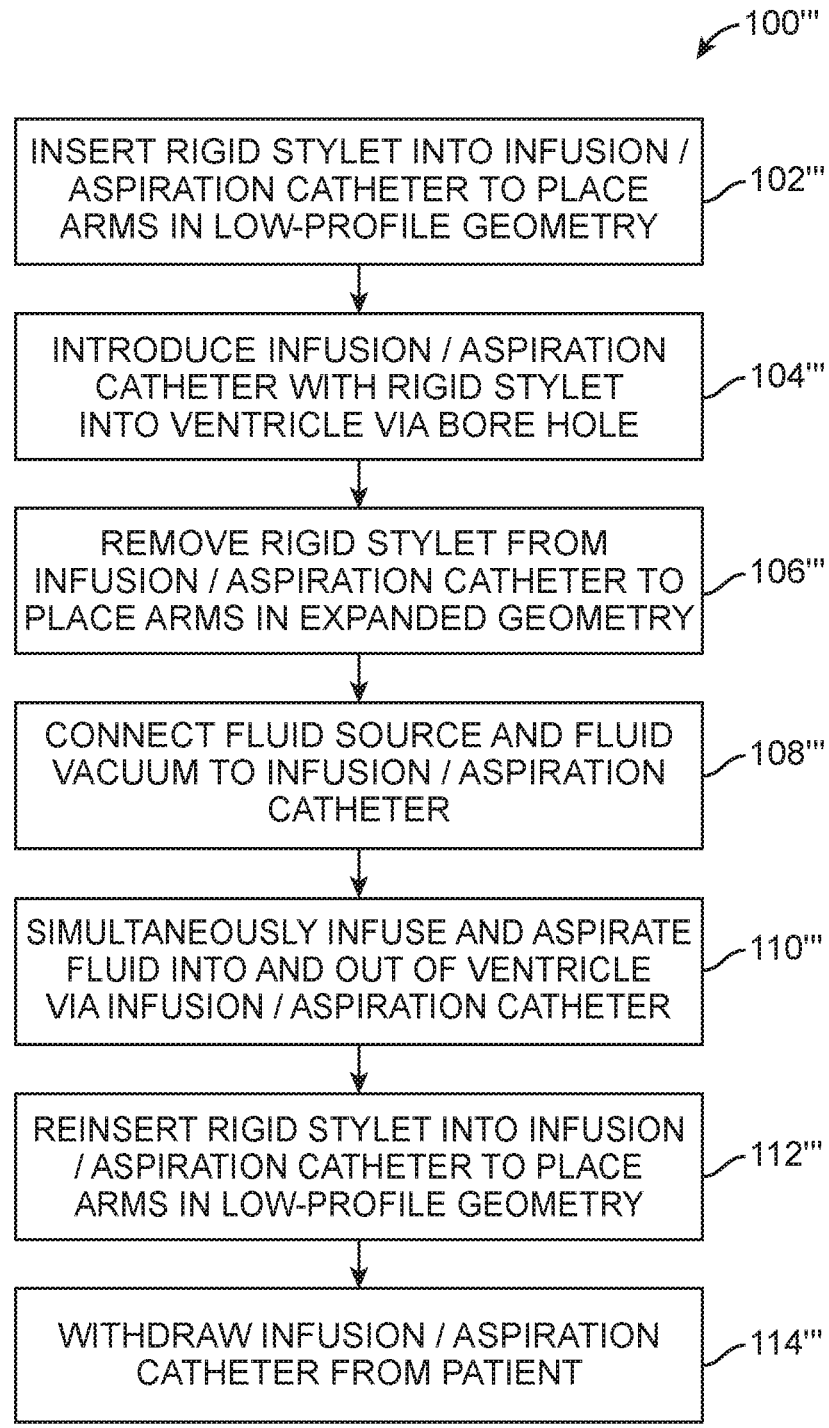
FIG. 19 is a flow diagram illustrating one method of using the infusion/aspiration system of FIG. 17 to treat an ICH within a brain of a patient.

Having described the structure and operation of the infusion/aspiration system 10''', one method 100''' of operating it to treat an anatomical cavity 82 of a patient 80 will now be described with respect to FIG. 19, as well as FIGS. 20A-20D. As with the previous exemplary method 100, in this method 100''', the anatomical cavity 82 is a ventricle within the cranium 84 of the patient 80, and the patient 80 has suffered a hemorrhagic stroke, resulting in a clot 86 within the ventricle 82, such that the treatment of the patient 80 involves infusing fluid comprising rt-PA, into the ventricle 82 to dissolve the clot 86, and the rt-PA fluid, along with the dissolved clot 86, is aspirated out from the ventricle 82.

This method 100''' does not require the use of an introducer sheath 12, and therefore, such introducer sheath 12 is not introduced into the ventricle 82. Instead, the rigid stylet 64 is inserted through the central aspiration lumen 34b of the infusion/aspiration catheter 14''', and then the distal end of the rigid stylet 64 is introduced through the aperture 66 of the distal hub 42 to straighten the arms 12 into the low-profile geometry (step 102''') (see FIG. 20A). Next, the infusion/aspiration catheter 14''', along with the rigid stylet 64, is introduced into the ventricle 82 through the conventional bore hole 88 formed through the cranium 84 (step 104''') (see FIG. 20B). Next, the rigid stylet 64 is removed from the central aspiration lumen 34b of the infusion/aspiration catheter 14''', thereby allowing the arms 12 to expand outward into the expanded geometry (step 106''') (see FIG. 20C). Next, the fluid source 16 and the vacuum source 18 are connected to the respective infusion connector(s) 56a and aspiration connector 56b of the infusion/aspiration catheter 14 (step 108''').

Figure 20A:
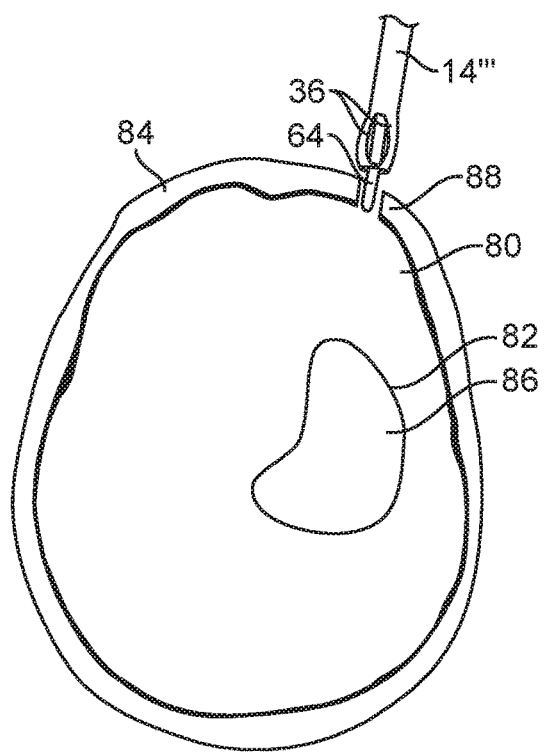
FIGS. 20A-20D are plan views illustrating the use of the infusion/aspiration system of FIG. 17 to treat the ICH within the brain of the patient in accordance with the method of FIG. 19.
Figure 20B:
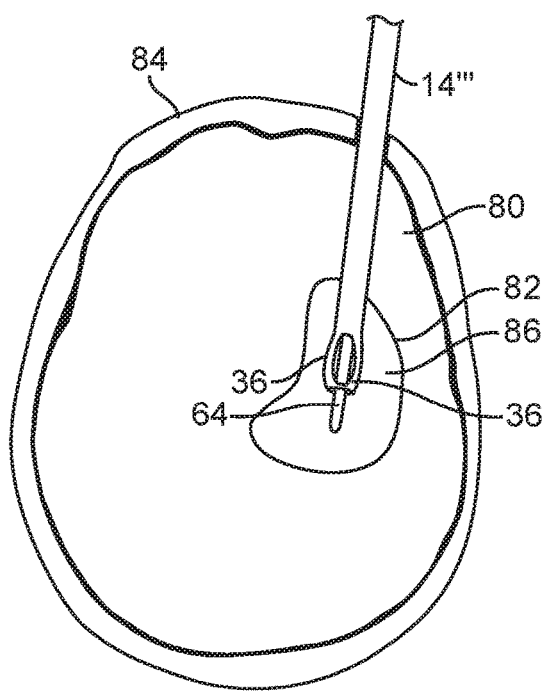
Figure 20C:
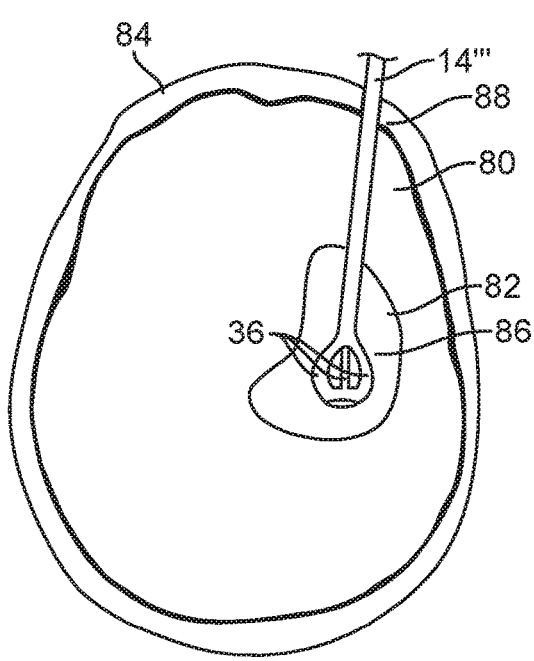
Figure 20D:
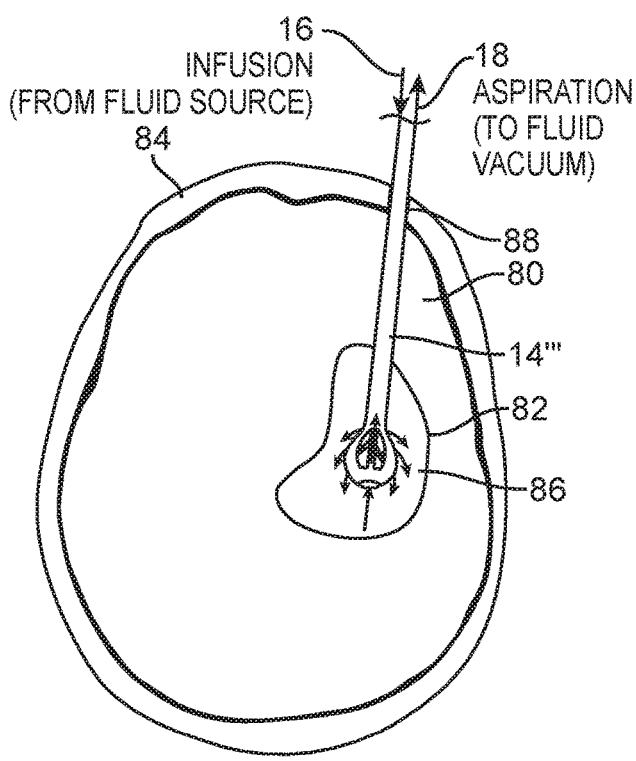

Fluid comprising rt-PA (or other therapeutic solution) is then simultaneously infused into and aspirated from the ventricle 82 (step 110''') (see FIG. 20D). That is, rt-PA fluid will flow from the fluid source 16 into the infusion connector(s) 56a, through the three infusion lumens 34a within the elongate catheter body 28, through the lumens 44, and out the fluid ports 46, of the three arms 36, thereby dissolving the clot 86, and simultaneously, the rt-PA fluid and any dissolved clot 86, will flow into the distal fluid port 80, through the central aspiration lumen 34b, within the elongate catheter body 28, out of the aspiration connector 56b, and into the vacuum source 18.

The method 100''' may optionally comprise aspirating by draining the fluid by disconnecting one or both of the fluid source 16 and aspiration pump 18 from one or more of the connectors 56. That is, fluid will drain into the fluid ports 46, and through the lumen(s) 44, of the arm(s) 36, and/or into the distal port 80, through the lumen(s) 34 within the elongate catheter body 28, out of the connector(s) 56, and into a basin under atmospheric pressure (or optionally using an automated system to infuse, aspirate, and/or drain).

After the procedure is completed, the rigid stylet 64 is reinserted through the central aspiration lumen 34b of the infusion/aspiration catheter 14''' until the distal end of the rigid stylet 64, and then the distal end of the rigid stylet 64 is introduced through the aperture 66 of the distal hub 42 to straighten the arms 12 into the low-profile geometry. The infusion/aspiration catheter 14 can then be removed from the patient.

Although the embodiments described herein lend themselves well to the simultaneous infusion and aspiration of fluid into and out of an anatomical cavity, it should be appreciated that in some circumstances, such simultaneous infusion and aspiration of fluid may not be needed. In this case, the infusion and aspiration of the fluid into and out of the anatomical cavity can be staged (i.e., performed serially). For example, with respect to the infusion/aspiration catheters 10, 10', and 10'', all three lumens 34 of the elongated catheter body 28 can be used as infusion lumens to deliver the rt-PA (or other therapeutic solution) into the anatomical cavity, and then all three lumens 34 of the elongated catheter body 28 can be used as aspiration lumens to aspirate the rt-PA (or other therapeutic solution) from the anatomical cavity. Thus, all of the lumens 34 may be configured for infusion at once, and likewise, all of the lumens 34 may be configured for aspiration at once. In this manner, infusion out of the lumens 44 of all three of the arms 36 will advantageously deliver the rt-PA to a larger more spread out region. The lumens 34 may also be switched between aspiration and infusion into any configuration at will or via an automated control system. In this case, a single connector 56 can be affixed to the proximal end 30 of the elongate catheter body 28 in fluid communication with the lumens 34 of the elongate catheter body 28, such that the fluid source 16 can be connected to the single connector 56, and after the infusion process is completed, the aspiration pump 18 can be connected to the same connector 56.

Although particular embodiments of the disclosed inventions have been shown and described, it will be understood that it is not intended to limit the disclosed inventions to the preferred embodiments, and it will be obvious to those skilled in the art that various changes and modifications may be made without departing from the scope of the disclosed inventions as defined by the claims.

What is claimed is:

1. A method of treating an anatomical cavity within a brain of a patient using an infusion/aspiration catheter, wherein the patient has clot residing within the anatomical cavity as a result of a hemorrhagic stroke suffered by the patient, the infusion/aspiration catheter comprising an elongate catheter body having a proximal end, a distal end, and a plurality of independent lumens extending between the proximal end and the distal end, a plurality of arms respectively having proximal ends affixed together at the distal end of elongate catheter body, each of the arms having a lumen in fluid communication with a respective one of the independent lumens of the elongate catheter body, each of the arms having at least one fluid port in fluid communication with the lumen of the respective arm, and at least one connector affixed to the proximal end of the elongate catheter body in fluid communication with the independent lumens of the elongate catheter body, the method comprising:
   introducing the infusion/aspiration catheter into the patient, such that the plurality of arms reside within the anatomical cavity;
   delivering a fluid comprising recombinant tissue plasminogen activator (rt-PA) into the at least one of the connector, such that fluid exits the at least one fluid port of at least one of the arms, thereby infusing the anatomical cavity with the fluid, and the infused rt-PA dissolves the clot; and
   aspirating the fluid, along with dissolved clot, into the at least one fluid port of at least one of the arms, such that the fluid, along with the dissolved clot, exits the at least one connector.

2. The method of claim 1, wherein the at least one connector comprises a plurality of connectors in fluid communication with the independent lumens of the elongate catheter body, and wherein the fluid is simultaneously infused into and aspirated from the anatomical cavity via different ones of the connectors.

3. The method of claim 1, wherein the fluid is sequentially infused into and aspirated from the anatomical cavity via the same ones of the at least one connector.

4. The method of claim 1, wherein the anatomical cavity is a ventricle within the brain of the patient or a region where clot has displaced brain tissue of the patient.

5. The method of claim 4, wherein the infusion/aspiration catheter is introduced into the anatomical cavity through a burr hole in a cranium of the patient.

6. The method of claim 1, further comprising expanding the arms outward within the anatomical cavity.

7. The method of claim 6, further comprising placing an introducer sheath within the anatomical cavity, wherein the plurality of arms is pre-shaped to expand outward in the absence of an external force, and wherein introducing the infusion/aspiration catheter into the patient comprises introducing the infusion/aspiration catheter through the introducer sheath, such that the introducer sheath applies an external force to the plurality of arms to straighten the arms, and deploying plurality of arms from the introducer sheath, such that the external force is released from the plurality of arms, thereby allowing the arms to expand outward.

8. The method of claim 6, wherein an actuation wire is affixed to a distal hub of the infusion/aspiration catheter, the method further comprising displacing the actuation wire distally relative to the infusion/aspiration catheter to straighten the arms while introducing the infusion/aspiration catheter into the anatomical cavity, and displacing the actuation wire proximally relative to the infusion/aspiration catheter to expand the arms outward within the anatomical cavity.

9. The method of claim 1, wherein the elongate catheter body further has a central lumen extending between the proximal end and distal end of the elongate catheter body, wherein introducing the infusion/aspiration catheter into the anatomical cavity comprises disposing a rigid stylet within the central lumen of the elongate catheter body.

10. A method of treating an anatomical cavity within a brain of a patient using an infusion/aspiration catheter, wherein the patient has clot residing within the anatomical cavity as a result of a hemorrhagic stroke suffered by the patient, the infusion/aspiration catheter comprising an elongate catheter body having a proximal end, a distal end, at least one infusion lumen, and an aspiration lumen extending between the proximal end and the distal end, the aspiration lumen terminating in a distal fluid port at the distal end of the elongate catheter body, a plurality of arms respectively having proximal ends affixed together at the distal end of elongate catheter body, the distal fluid port of the elongate catheter body being between the proximal ends of the plurality of arms, the arms having lumens in fluid communication with the at least one infusion lumen, each of the arms having at least one fluid port in fluid communication with the lumen of the respective arm, at least one infusion connector affixed to the proximal end of the elongate catheter body in fluid communication with the at least one infusion lumen, and an aspiration connector affixed to the proximal end of the elongate catheter body in fluid communication with the at least one aspiration lumen, the method comprising:

introducing the infusion/aspiration catheter into the patient, such that the plurality of arms reside within the anatomical cavity;

delivering a fluid comprising recombinant tissue plasminogen activator (rt-PA) into the at least one of the infusion connector, such that fluid exits the at least one fluid port of each of the plurality of arms, thereby infusing the anatomical cavity with the fluid and the infused rt-PA dissolves the clot; and aspirating the fluid, along with dissolved clot, into the distal fluid port of the elongate catheter body, such that the fluid, along with dissolved clot, exits the aspiration connector.

11. The method of claim 10, wherein the fluid is simultaneously infused into and aspirated from the anatomical cavity.

12. The method of claim 10, wherein the fluid is sequentially infused into and aspirated from the anatomical cavity.

13. The method of claim 10, wherein the anatomical cavity is a ventricle within the brain of the patient or a region where clot has displaced brain tissue of the patient, and wherein the infusion/aspiration catheter is introduced into the anatomical cavity through a burr hole in a cranium of the patient.

14. The method of claim 10, further comprising
    expanding the arms outward within the anatomical cavity, and
    placing an introducer sheath within the anatomical cavity, wherein the plurality of arms is pre-shaped to expand outward in the absence of an external force, and wherein introducing the infusion/aspiration catheter into the patient comprises introducing the infusion/aspiration catheter through the introducer sheath, such that the introducer sheath applies an external force to the plurality of arms to straighten the arms, and deploying plurality of arms from the introducer sheath, such that the external force is released from the plurality of arms, thereby allowing the arms to expand outward.

15. The method of claim 10, wherein an actuation wire is affixed to a distal hub of the infusion/aspiration catheter, the method further comprising
    expanding the arms outward within the anatomical cavity, and
    displacing the actuation wire distally relative to the infusion/aspiration catheter to straighten the arms while introducing the infusion/aspiration catheter into the anatomical cavity, and displacing the actuation wire proximally relative to the infusion/aspiration catheter to expand the arms outward within the anatomical cavity.

16. The method of claim 10, wherein introducing the infusion/aspiration catheter into the anatomical cavity comprises disposing a rigid stylet within the central lumen of the elongate catheter body.

17. The method of claim 1, wherein the arms are electrodeless, and the clot is removed from the brain without performing an ablation procedure within the anatomical cavity.

18. The method of claim 10, wherein the arms are electrodeless, and the clot is removed from the brain without performing an ablation procedure within the anatomical cavity.

\* \* \* \* \*